United States Patent
Wilson et al.

(10) Patent No.: US 9,505,826 B2
(45) Date of Patent: Nov. 29, 2016

(54) MODIFIED ANTIBODY WITH IMPROVED HALF-LIFE

(75) Inventors: David Wilson, Fremont, CA (US); Tetsuya Taura, Palo Alto, CA (US)

(73) Assignee: Teva Pharmaceuticals Australia Pty Ltd, Macquarie Park, NSW (AU)

( * ) Notice: Subject to any disclaimer, the term of this patent is extended or adjusted under 35 U.S.C. 154(b) by 462 days.

(21) Appl. No.: 13/996,733

(22) PCT Filed: Dec. 22, 2011

(86) PCT No.: PCT/AU2011/001662
§ 371 (c)(1),
(2), (4) Date: Jun. 21, 2013

(87) PCT Pub. No.: WO2012/083370
PCT Pub. Date: Jun. 28, 2012

(65) Prior Publication Data
US 2013/0281677 A1   Oct. 24, 2013

Related U.S. Application Data

(60) Provisional application No. 61/425,858, filed on Dec. 22, 2010.

(51) Int. Cl.
| | | |
|---|---|---|
| C07K 16/00 | (2006.01) | |
| C12P 21/08 | (2006.01) | |
| A61K 39/395 | (2006.01) | |
| A61K 39/40 | (2006.01) | |
| C07K 16/28 | (2006.01) | |
| C07K 1/00 | (2006.01) | |

(52) U.S. Cl.
CPC ......... C07K 16/00 (2013.01); C07K 16/2803 (2013.01); *C07K 2317/52* (2013.01); *C07K 2317/90* (2013.01)

(58) Field of Classification Search
None
See application file for complete search history.

(56) References Cited

U.S. PATENT DOCUMENTS

| 7,083,784 B2 | 8/2006 | Dall'Acqua et al. |
| RE39,548 E | 4/2007 | Bodmer et al. |
| 8,092,804 B2 * | 1/2012 | Eriksson et al. ............ 424/143.1 |
| 2004/0110226 A1 * | 6/2004 | Lazar ..................... C07K 16/00 435/7.1 |
| 2009/0202568 A1 * | 8/2009 | Eriksson ............ C07K 16/2866 424/173.1 |
| 2010/0278839 A1 | 11/2010 | Powell et al. |
| 2013/0281677 A1 * | 10/2013 | Wilson ............... C07K 16/2803 530/389.1 |

FOREIGN PATENT DOCUMENTS

| WO | 2008134046 | 11/2008 |
| WO | 20100703456 | 6/2010 |
| WO | 2010085682 | 7/2010 |

OTHER PUBLICATIONS

Martin et al. Molecular Cell 2001 7:867-877.*
Shields et al. JBC, 2001. 276;(9):6591-6604.*
Janeway et al., Immunology Third Edition, Garland Publishing Inc. 1997, Chapter 3, pp. 3:1-3:11.*
Rudikoff et al. PNAS 1982 vol. 79 p. 1979-1983.*
William E. Paul. Fundamental Immunology, 3rd ed. 1993, p. 242.*
Portolano et al., Journal of Immunology, 1993 150:880-887.*
Casset et al. BBRC(2003) 307, 198-205.*
Angal, S., et al., "A single amino acid substitution abolishes the heterogeneity of chimeric mouse/human (IgG4) antibody", Molecular Immunology, (1993), vol. 30, No. 1, pp. 105-108.
Hamann, P., et al., "An Anti-CD33 Antibody—Calicheamicin Conjugate for Treatment of Acute Myeloid Leukemia. Choice fof Linker", Bioconjugate Chem., 2002, vol. 13, pp. 40-46.
Kim, J., et al., "Catabolism of the Murine IgG1 Molecule: Evidence that Both CH2-CH3 Domain Interfaces are Required for Petsistence of IgG1 in the Circulation of Mice", Scand. J. Immunol., vol. 40, 1994, pp. 457-465.
Kim, J., et al., "Identifying amino acid residues that influence plasma clearance of murine IgG1 fragments by site-directed mutagenesis", Eur. J. Immunol., 1994, vol. 24, pp. 542-548.
Kim., J., et al., "Localization of the site of the murine IgG1 molecule that is involved in binding to the murine intestinal Fc receptor", Eur. J. Immunol., 1994, vol. 24, pp. 2429-2434.
Labrijn, A., et al., "Therapeutic IgG4 antibodies engage in Fab-arm exchange with endogenous human IgG4 in vivo", Nature Biotechnology, vol. 27, No. 8, Aug. 2009, pp. 767-773.
Marks, J.D., et al., "By-passing Immunization—Human Antibodies from V-gene Libraries Displayed on Phage", J. Mol. Biol., 1991, vol. 222, pp. 581-597.
Schuurman, J., et al., "The inter-heavy chain disulfide bonds of IgG4 are in equilibrium with intra-chain disulfide bonds", Molecular Immunology, 2001, vol. 38, pp. 1-8.
Zalevsky, J., et al., "Enhanced antibody half-life improves in vivo activity", Nature Biotechnology, published online Jan. 17, 2010, pp. 1-3.
International Search Report dated Feb. 14, 2012 issued in counterpart application PCT/AU2011/001662.

* cited by examiner

*Primary Examiner* — Chun Dahle
(74) *Attorney, Agent, or Firm* — Stradley Ronon Stevens & Young, LLP

(57) ABSTRACT

The present invention relates to antibodies, immunoglobulin constructs or immunoglobulin IgG4 fusion proteins whose in vivo half-lives are increased by the combination of (i) a modified IgG4 Fc region or FcRn binding domain thereof and (ii) a modified IgG4 hinge region sequence.

6 Claims, 10 Drawing Sheets

Sequence of hu39D10 heavy chain variable and constant region

EVQLVESGGGLVQPGGSLRLSCAVSGLSLTSNSVNWIRQAPGKGLEWVGLIWSNGDTDYNSAIK
SRFTISRDTSKSTVYLQMNSLRAEDTAVYYCAREYYGYFDYWGQGTLVTVSSASTKGPSVFPLA
PCSRSTSESTAALGCLVKDYFPEPVTVSWNSGALTSGVHTFPAVLQSSGLYSLSSVVTVPSSSL
GTKTYTCNVDHKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQKSLSLSLGK (SEQ
ID NO:2)

Sequence of native human IgG4 constant region

ASTKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPSCPAPEFLGGPSVFLFPPKPK
DTLMISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKS
LSLSLGK (SEQ ID NO:3)

Sequence of modified human IgG4 constant region (S228P)
(underline and bold: substituted amino acid residues)

ASTKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKS
LSLSLGK (SEQ ID NO:4)

Sequence of modified human IgG4 constant region (YTE)
(underline and bold: substituted amino acid residues)

ASTKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPSCPAPEFLGGPSVFLFPPKPK
DTLYITREPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKS
LSLSLGK (SEQ ID NO:5)

FIGURE 1A

Sequence of modified human IgG4 constant region (S228P + YTE)
(underline and bold: substituted amino acid residues)

ASTKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFPPKPK
DTLYITREPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKS
LSLSLGK (SEQ ID NO:6)

Sequence of hu39D10 heavy chain variable domain

EVQLVESGGGLVQPGGSLRLSCAVSGLSLTSNSVNWIRQAPGKGLEWVGLIWSNGDTDYNSAIK
SRFTISRDTSKSTVYLQMNSLRAEDTAVYYCAREYYGYFDYWGQGTLVTVSS (SEQ ID
NO:7)

Sequence of hu39D10 light chain variable and constant domain
(constant domain is underlined)

DIQMTQSPSSLSASVGDRVTITCLASEGISSYLAWYQQKPGKAPKLLIYGANSLQTGVPSRFSG
SGSATDYTLTISSLQPEDFATYYCQQSYKFPNTFGQGTKVEVK<u>RTVAAPSVFIFPPSDEQLKSG</u>
<u>TASVVCLLNNFYPREAKVQWKVDNALQSGNSQESVTEQDSKDSTYSLSSTLTLSKADYEKHKVY</u>
<u>ACEVTHQGLSSPVTKSFNRGEC</u> (SEQ ID NO:8)

FIGURE 1B

Sequence of human FcRn extra cellular domain

AESHLSLLYHLTAVSSPAPGTPAFWVSGWLGPQQYLSYNSLRGEAEPCGAWVWENQVS
WYWEKETTDLRIKEKLFLEAFKALGGKGPYTLQGLLGCELGPDNTSVPTAKFALNGEE
FMNFDLKQGTWGGDWPEALAISQRWQQQDKAANKELTFLLFSCPHRLREHLERGRGNL
EWKEPPSMRLKARPSSPGFSVLTCSAFSFYPPELQLRFLRNGLAAGTGQGDFGPNSDG
SFHASSSLTVKSGDEHHYCCIVQHAGLAQPLRVEL (SEQ ID NO:9)

FIGURE 2

Sequence of human β2-microglobulin mature domain

IQRTPKIQVYSRHPAENGKSNFLNCYVSGFHPSDIEVDLLKNGERIEKVEHSDLSFSK
DWSFYLLYYTEFTPTEKDEYACRVNHVTLSQPKIVKWDRDM (SEQ ID NO:10)

FIGURE 3

Sequence of huMab195 heavy chain variable and IgG4 version of constant region with S228P and YTE mutations
(bold and underline: substituted amino acid residues)

QVQLVQSGAEVKKPGSSVKVSCKASGYTFTDYNMHWVRQAPGQGLEWIGYIYPYNGGT
GYNQKFKSKATITADESTNTAYMELSSLRSEDTAVYYCARGRPAMDYWGQGTLVTVSS
ASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFLG
GPSVFLFPPKPKDTLYITRE**PEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLGK (SEQ ID NO:11)

Sequence of huMab195 light chain variable and constant domains

DIQMTQSPSSLSASVGDRVTITCRASESVDNYGISFMNWFQQKPGKAPKLLIYAASNQ
GSGVPSRFSGSGSGTDFTLTISSLQPDDFATYYCQQSKEVPWTFGQGTKVEIKRTVAA
PSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC (SEQ ID
NO:12)

FIGURE 6

Sequence of human CD33 extra cellular domain-Fc fusion

MDPNFWLQVQESVTVQEGLCVLVPCTFFHPIPYYDKNSPVHGYWFREGAIISRDSPVA
TNKLDQEVQEETQGRFRLLGDPSRNNCSLSIVDARRRDNGSYFFRMERGSTKYSYKSP
QLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGS
GKQETRAGVVAGHHHHHHLVPRGSTHTCPPCPAPELLGGPSVFLFPPKPKDTLMISRT
PEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHE
ALHNHYTQKSLSLSPGK (SEQ ID NO:13)

FIGURE 7

Sequence of hinge-Fc portion of native human IgG4 heavy chain

CPSCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKG
QPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK (SEQ ID NO:15)

Sequence of hinge-Fc portion of human IgG4 heavy chain with S228P and YTE mutations and lacking the C-terminal lysine
(bold and underline: substituted amino acid residues)

CPPCPAPEFLGGPSVFLFPPKPKDTLYITREPEVTCVVVDVSQEDPEVQFNWYVDGVE
VHNAKTKPREEQFNSTYRVVSVLTVLHQDWLNGKEYKCKVSNKGLPSSIEKTISKAKG
QPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLG (SEQ ID NO:14)

FIGURE 9

SEQUENCE LISTING

```
<160> NUMBER OF SEQ ID NOS: 15

<210> SEQ ID NO 1
<211> LENGTH: 5
<212> TYPE: PRT
<213> ORGANISM: Homo sapiens

<400> SEQUENCE: 1

Cys Pro Ser Cys Pro
1               5

<210> SEQ ID NO 2
<211> LENGTH: 443
<212> TYPE: PRT
<213> ORGANISM: artificial sequence
<220> FEATURE:
<223> OTHER INFORMATION: sequence of hu39D10 heavy chain variable and
      constant region

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Ser Leu Thr Ser Asn
            20                  25                  30

Ser Val Asn Trp Ile Arg Gln Ala Pro Gly Lys Gly Leu Glu Trp Val
        35                  40                  45

Gly Leu Ile Trp Ser Asn Gly Asp Thr Asp Tyr Asn Ser Ala Ile Lys
    50                  55                  60

Ser Arg Phe Thr Ile Ser Arg Asp Thr Ser Lys Ser Thr Val Tyr Leu
65                  70                  75                  80

Gln Met Asn Ser Leu Arg Ala Glu Asp Thr Ala Val Tyr Tyr Cys Ala
                85                  90                  95

Arg Glu Tyr Tyr Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 3
<211> LENGTH: 327
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

-continued

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 4
<211> LENGTH: 327
<212> TYPE: PRT
<213> ORGANISM: artificial sequence
<220> FEATURE:
<223> OTHER INFORMATION: sequence of modified human IgG4 constant region

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110
```

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 327
<212> TYPE: PRT
<213> ORGANISM: artificial sequence
<220> FEATURE:
<223> OTHER INFORMATION: sequence of modified human IgG4 constant region

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 6
<211> LENGTH: 327
<212> TYPE: PRT
<213> ORGANISM: artificial sequence
<220> FEATURE:
<223> OTHER INFORMATION: sequence of modified human IgG4 constant region

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

-continued

```
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 7
<211> LENGTH: 116
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15
Ser Leu Arg Leu Ser Cys Ala Val Ser Gly Leu Ser Leu Thr Ser Asn
            20                  25                  30
Ser Val Asn Trp Ile Arg Gln Ala Pro Gly Lys Gly Leu Glu Trp Val
        35                  40                  45
Gly Leu Ile Trp Ser Asn Gly Asp Thr Asp Tyr Asn Ser Ala Ile Lys
    50                  55                  60
Ser Arg Phe Thr Ile Ser Arg Asp Thr Ser Lys Ser Thr Val Tyr Leu
65                  70                  75                  80
Gln Met Asn Ser Leu Arg Ala Glu Asp Thr Ala Val Tyr Tyr Cys Ala
                85                  90                  95
Arg Glu Tyr Tyr Gly Tyr Phe Asp Tyr Trp Gly Gln Gly Thr Leu Val
            100                 105                 110
Thr Val Ser Ser
        115

<210> SEQ ID NO 8
<211> LENGTH: 214
<212> TYPE: PRT
<213> ORGANISM: artificial sequence
<220> FEATURE:
<223> OTHER INFORMATION: sequence of hu39D10 light chain variable domain

<400> SEQUENCE: 8

Asp Ile Gln Met Thr Gln Ser Pro Ser Ser Leu Ser Ala Ser Val Gly
1               5                   10                  15
Asp Arg Val Thr Ile Thr Cys Leu Ala Ser Glu Gly Ile Ser Ser Tyr
            20                  25                  30
```

```
Leu Ala Trp Tyr Gln Gln Lys Pro Gly Lys Ala Pro Lys Leu Leu Ile
            35                  40                  45

Tyr Gly Ala Asn Ser Leu Gln Thr Gly Val Pro Ser Arg Phe Ser Gly
 50                  55                  60

Ser Gly Ser Ala Thr Asp Tyr Thr Leu Thr Ile Ser Ser Leu Gln Pro
 65                  70                  75                  80

Glu Asp Phe Ala Thr Tyr Tyr Cys Gln Gln Ser Tyr Lys Phe Pro Asn
                 85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 9
<211> LENGTH: 267
<212> TYPE: PRT
<213> ORGANISM: Homo sapiens

<400> SEQUENCE: 9

Ala Glu Ser His Leu Ser Leu Leu Tyr His Leu Thr Ala Val Ser Ser
 1               5                  10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
            35                  40                  45

Gly Ala Trp Val Trp Glu Asn Gln Val Ser Trp Tyr Trp Glu Lys Glu
 50                  55                  60

Thr Thr Asp Leu Arg Ile Lys Glu Lys Leu Phe Leu Glu Ala Phe Lys
 65                  70                  75                  80

Ala Leu Gly Gly Lys Gly Pro Tyr Thr Leu Gln Gly Leu Leu Gly Cys
                 85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
            115                 120                 125

Gly Asp Trp Pro Glu Ala Leu Ala Ile Ser Gln Arg Trp Gln Gln Gln
130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190
```

```
Phe Ser Val Leu Thr Cys Ser Ala Phe Ser Phe Tyr Pro Pro Glu Leu
            195                 200                 205

Gln Leu Arg Phe Leu Arg Asn Gly Leu Ala Ala Gly Thr Gly Gln Gly
            210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
            245                 250                 255

Ala Gly Leu Ala Gln Pro Leu Arg Val Glu Leu
            260                 265

<210> SEQ ID NO 10
<211> LENGTH: 99
<212> TYPE: PRT
<213> ORGANISM: artificial sequence
<220> FEATURE:
<223> OTHER INFORMATION: sequence of human beta-2 microglobulin mature
      domain

<400> SEQUENCE: 10

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 11
<211> LENGTH: 443
<212> TYPE: PRT
<213> ORGANISM: artificial sequence
<220> FEATURE:
<223> OTHER INFORMATION: sequence of huMab195 heavy chain variable and
      IgG4 modified constant and hinge region

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110
```

```
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
        195                 200                 205
Lys Val Asp Lys Arg Val Glu Ser Lys Tyr Gly Pro Pro Cys Pro Pro
    210                 215                 220
Cys Pro Ala Pro Glu Phe Leu Gly Gly Pro Ser Val Phe Leu Phe Pro
225                 230                 235                 240
Pro Lys Pro Lys Asp Thr Leu Tyr Ile Thr Arg Glu Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly Lys
        435                 440

<210> SEQ ID NO 12
<211> LENGTH: 218
<212> TYPE: PRT
<213> ORGANISM: artificial sequence
<220> FEATURE:
<223> OTHER INFORMATION: sequence of huMab195 light chain variable and
      constant domains

<400> SEQUENCE: 12

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Ser Val Asp Asn Tyr
            20                  25                  30
```

```
Gly Ile Ser Phe Met Asn Trp Phe Gln Gln Lys Pro Gly Lys Ala Pro
            35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Asp Asp Phe Ala Thr Tyr Tyr Cys Gln Gln Ser Lys
                 85                  90                  95

Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 13
<211> LENGTH: 481
<212> TYPE: PRT
<213> ORGANISM: artificial sequence
<220> FEATURE:
<223> OTHER INFORMATION: sequence of human CD33 extracellular domain Fc
      fusion

<400> SEQUENCE: 13

Met Asp Pro Asn Phe Trp Leu Gln Val Gln Glu Ser Val Thr Val Gln
 1               5                  10                  15

Glu Gly Leu Cys Val Leu Val Pro Cys Thr Phe Phe His Pro Ile Pro
            20                  25                  30

Tyr Tyr Asp Lys Asn Ser Pro Val His Gly Tyr Trp Phe Arg Glu Gly
             35                  40                  45

Ala Ile Ile Ser Arg Asp Ser Pro Val Ala Thr Asn Lys Leu Asp Gln
 50                  55                  60

Glu Val Gln Glu Glu Thr Gln Gly Arg Phe Arg Leu Leu Gly Asp Pro
 65                  70                  75                  80

Ser Arg Asn Asn Cys Ser Leu Ser Ile Val Asp Ala Arg Arg Arg Asp
                 85                  90                  95

Asn Gly Ser Tyr Phe Phe Arg Met Glu Arg Gly Ser Thr Lys Tyr Ser
            100                 105                 110

Tyr Lys Ser Pro Gln Leu Ser Val His Val Thr Asp Leu Thr His Arg
            115                 120                 125

Pro Lys Ile Leu Ile Pro Gly Thr Leu Glu Pro Gly His Ser Lys Asn
            130                 135                 140

Leu Thr Cys Ser Val Ser Trp Ala Cys Glu Gln Gly Thr Pro Pro Ile
145                 150                 155                 160

Phe Ser Trp Leu Ser Ala Ala Pro Thr Ser Leu Gly Pro Arg Thr Thr
```

```
                    165                 170                 175
His Ser Ser Val Leu Ile Ile Thr Pro Arg Pro Gln Asp His Gly Thr
            180                 185                 190

Asn Leu Thr Cys Gln Val Lys Phe Ala Gly Ala Gly Val Thr Thr Glu
            195                 200                 205

Arg Thr Ile Gln Leu Asn Val Thr Tyr Val Pro Gln Asn Pro Thr Thr
            210                 215                 220

Gly Ile Phe Pro Gly Asp Gly Ser Gly Lys Gln Glu Thr Arg Ala Gly
225                 230                 235                 240

Val Val Ala Gly His His His His His His Leu Val Pro Arg Gly Ser
            245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
            290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
            370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
            450                 455                 460

Ala Leu His Asn His Tyr Thr Gln Lys Ser Leu Ser Leu Ser Pro Gly
465                 470                 475                 480

Lys

<210> SEQ ID NO 14
<211> LENGTH: 221
<212> TYPE: PRT
<213> ORGANISM: artificial sequence
<220> FEATURE:
<223> OTHER INFORMATION: sequence of hinge-Fc portion of human IgG4
      heavy chain with S228P and YTE mutations and lacking the
      C-terminal lysine

<400> SEQUENCE: 14

Cys Pro Pro Cys Pro Ala Pro Glu Phe Leu Gly Gly Pro Ser Val Phe
1               5                   10                  15

Leu Phe Pro Pro Lys Pro Lys Asp Thr Leu Tyr Ile Thr Arg Glu Pro
            20                  25                  30
```

```
Glu Val Thr Cys Val Val Asp Val Ser Gln Glu Asp Pro Glu Val
         35                  40                  45

Gln Phe Asn Trp Tyr Val Asp Gly Val Glu Val His Asn Ala Lys Thr
 50                  55                  60

Lys Pro Arg Glu Glu Gln Phe Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Gly Leu Pro Ser Ser Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Gln Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly
    210                 215                 220

<210> SEQ ID NO 15
<211> LENGTH: 222
<212> TYPE: PRT
<213> ORGANISM: Homo sapiens

<400> SEQUENCE: 15

Cys Pro Ser Cys Pro Ala Pro Glu Phe Leu Gly Gly Pro Ser Val Phe
 1               5                  10                  15

Leu Phe Pro Pro Lys Pro Lys Asp Thr Leu Met Ile Ser Arg Thr Pro
             20                  25                  30

Glu Val Thr Cys Val Val Asp Val Ser Gln Glu Asp Pro Glu Val
         35                  40                  45

Gln Phe Asn Trp Tyr Val Asp Gly Val Glu Val His Asn Ala Lys Thr
 50                  55                  60

Lys Pro Arg Glu Glu Gln Phe Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Gly Leu Pro Ser Ser Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Gln Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190
```

```
Gln Glu Gly Asn Val Phe Ser Cys Ser Val Met His Glu Ala Leu His
            195                 200                 205

Asn His Tyr Thr Gln Lys Ser Leu Ser Leu Ser Leu Gly Lys
210                 215                 220
```

MODIFIED ANTIBODY WITH IMPROVED HALF-LIFE

RELATED APPLICATIONS

This application is the U.S. National Phase of International Application No. PCT/AU2011/001662, filed on Dec. 22, 2011, and claims priority to U.S. Provisional Application No. 61/425,858 filed on Dec. 22, 2010, the entire contents of each application are herein incorporated by reference for all purposes.

REFERENCE TO A SEQUENCE LISTING

This application includes a Sequence Listing submitted electronically as a text file named 511513_ST25.txt, created on Jun. 18, 2013 with a size of 36,000 bytes. The Sequence Listing is incorporated by reference herein.

FIELD OF THE INVENTION

The present invention relates to antibodies, immunoglobulin constructs or immunoglobulin IgG4 fusion proteins whose in vivo half-lives are increased by the combination of (i) a modified IgG4 Fc region or FcRn binding domain thereof and (ii) a modified IgG4 hinge region sequence.

BACKGROUND OF THE INVENTION

IgG is the most prevalent immunoglobulin class in human and other mammals and is utilised in various types of immunotherapies and diagnostic procedures. One critical issue in these therapies is the period of persistence of immunoglobulins in the circulation. The rate of clearance of an administered immunoglobulin directly affects the amount and frequency of dosage of the immunoglobulin. Studies of IgG catabolism in the circulation have identified the portions of the IgG constant domain that control IgG metabolism, including the rate of IgG degradation in the serum through interactions with FcRn (Fc receptor neonate). Increased binding affinity for FcRn increases the circulating (or serum) half-life of an IgG (see for example, Kim et al., Eur J Immunol., 24:2429 (1994)). Methods for obtaining physiologically active molecules whose half-lives are modified by introducing an FcRn-binding polypeptide into the molecules are described, for example in WO 97/43316, U.S. Pat. Nos. 5,869,046, 5,747,035, WO 96/32478. Methods for fusing the molecules to antibodies or FcRn-binding domain fragments thereof are described for example in WO 99/43713. However, the above documents do not disclose specific mutants in the IgG constant domain that affect half-life.

The modification of IgG molecules by amino acid substitution, addition or deletion to increase or reduce affinity for FcRn is disclosed in WO 98/23289, however this document does not list any specific mutants that exhibit either longer or shorter in vivo half-lives.

One mutant of the mouse IgG1 that has been shown to increase circulating half-life is the triple mutation Thr252Ala, Thr254Ser and Thr256Phe described for example in WO 97/34631. MedImmune (U.S. Pat. No. 7,083,784) have demonstrated that, in the context of human IgG1, modifications of one or more of amino acid residues 251-256, 285-290, and 308-314, within the CH2 domain and amino acid residues 385-389 and 428-436 within the CH3 domain may increase the affinity of the constant domains for FcRn and hence increase circulating half-life. In particular, they demonstrated that a triple mutation M252Y, S254T and T256E, designated "YTE" in the Fc of a human IgG1 isotype antibody can increase the circulating half-life of antibodies about 2-3 fold in non-human primates.

Characteristics of IgG4 Isotype Antibodies

IgG4 differs from other human IgG isotypes in that upon SDS-PAGE under non-reducing conditions, two protein species are observed, the major species being tetrameric IgG (H2L2, that is, two heavy chains and two light chains) and a second minor species being a "half immunoglobulin" containing a single heavy chain and a single light chain (HL). These findings indicate heterogeneity in disulphide bond formation between the two heavy chains in the hinge region. Furthermore, when different human IgG4s with different antigen-binding specificities are mixed together, the individual IgG4 molecules are able to dissociate into half immunoglobulins (HL) and which then re-associate to form tetrameric IgG (H2L2) that bind to two different antigens (bispecific antibodies). It is believed that the HL species is a major intermediate in the assembly of IgG4. Analysis of the hinge sequences of human IgG heavy chains suggested that the presence of serine at residue 228 (also referred to in some publications as residue 241; for the avoidance of doubt, this refers to the serine in the center of the IgG4 hinge region sequence CPSCP (SEQ ID NO:1)) of IgG4 (according to the numbering system of Kabat et al., Sequences of Proteins of Immunological Interest 4$^{th}$ Edition. Washington D.C. United States Department of Health and Human Services) may be the cause of the heterogeneity. When this residue in IgG4 is modified from serine to proline (the residue naturally found at that position in IgG1 and IgG2), it leads to the production of homogenous antibody with extended serum half-life (Angal S et al., Molecular Immunology vol 30, no 1:105-108 (1993); Labrijn et al, Nature Biotechnology vol 27, no 8:767-771; Schuurman J et al., Molecular Immunology 38 (2001) 1-8).

There is an ongoing need to generate antibodies for therapeutic purposes with enhanced properties, such as an enhanced circulating half-life.

SUMMARY OF THE INVENTION

The present invention relates to molecules, in particular antibodies, immunoglobulin constructs and immunoglobulin IgG4 fusion proteins whose in vivo half-lives are increased by the combination of (i) an Fc region or FcRn binding domain region comprising an IgG4 isotype sequence which has been modified, and (ii) a modified IgG4 hinge region sequence. Specifically, these molecules have amino acid modifications, such as mutations, that increase the affinity of the Fc or heavy chain CH2 and CH3 constant regions for the FcRn and hence its circulating half-life in a subject. Moreover, the molecules include a modified IgG4 hinge region sequence which abrogates the formation of mixed heterodimers which is typical of IgG4 isotype antibodies.

The invention is based on the surprising discovery that the above combination of the modifications increases the circulating half-life of the molecule relative to its wild-type unmodified counterpart substantially longer than either the Fc region modification(s) or hinge region modification alone. Moreover, the combination of modifications results in a supra-additive (synergistic) lengthening of half-life. Because any modification in a human protein-based drug (including a protein comprising a human antibody constant region) increases the risk of inducing an anti-drug immune response in a patient, it is generally advisable to limit the number of such mutations to limit the presumably additively increased risk of each such mutation with respect to inducing such immune responses against the drug. However, due to the surprising results described herein that the combination of the two classes of substitutions (Fc modifications and hinge modifications) results in a supra-additive effect in increasing the circulating half-life of IgG4 antibodies. Consequently, this combination provides an unexpected advantage which can overcome a theoretical disadvantage relating to increasing the incidence of promoting anti-drug immune reactions. The advantages of increasing half-life of a molecule will be immediately evident to the person skilled in the art. Such benefits include lower dosing and/or frequency of administration which lowers the risk of adverse events in a subject and reduces costs. Accordingly, such immunoglobulins with increased half-life are of significant pharmaceutical importance.

Furthermore, because the molecules comprise IgG4 isotype constant domains and an IgG4 hinge region, the molecules exhibit no or minimal effector function in vivo.

Accordingly, in one embodiment, the present invention provides an isolated antibody, immunoglobulin construct or immunoglobulin IgG4 fusion protein with increased in vivo half-life, comprising:

(i) a human IgG4 Fc region or the FcRn binding domain thereof modified relative to a corresponding unmodified IgG4 Fc region or FcRn binding domain thereof to comprise substitutions at one or more of amino acid residues 251-256 numbered according to the EU index as in Kabat; and (ii) a human IgG4 core hinge region sequence comprising a substitution of the serine residue within the amino acid sequence CPSCP (SEQ ID NO:1) to proline;

wherein the in vivo half-life of the modified antibody, immunoglobulin construct or immunoglobulin IgG4 fusion protein is increased compared with the corresponding unmodified antibody, immunoglobulin construct or immunoglobulin IgG4 fusion protein.

The increased in vivo half-life of the antibody, immunoglobulin construct or immunoglobulin IgG4 fusion protein is determined by reference to the half life of a corresponding human IgG4 antibody, immunoglobulin construct or immunoglobulin IgG4 fusion protein which lacks the above substitutions.

The present invention also provides an isolated antibody, immunoglobulin construct or immunoglobulin IgG4 fusion protein with increased in vivo half-life, comprising:

(i) a human IgG4 Fc region or the FcRn binding domain thereof modified relative to a corresponding unmodified IgG4 Fc region or FcRn binding domain thereof to comprise substitutions M252Y, S254T and T256E numbered according to the EU index as in Kabat; and (ii) a human IgG4 core hinge region sequence comprising the amino acid substitution S228P according to the EU index as in Kabat;

wherein the in vivo half-life of the modified antibody, immunoglobulin construct or immunoglobulin IgG4 fusion protein is increased compared with the corresponding unmodified antibody, immunoglobulin construct or immunoglobulin IgG4 fusion protein.

The antibody according to the invention may be a chimeric antibody, human antibody, humanized antibody, a Superhumanised® antibody, a de-immunized antibody or a veneered antibody.

In one example, the present invention provides an isolated antibody with increased in vivo half-life, comprising:

(i) a human or humanised Fab;

(ii) a human IgG4 Fc region or the FcRn binding domain thereof modified relative to a corresponding unmodified IgG4 Fc region or FcRn binding domain thereof to comprise substitutions at one or more of amino acid residues 251-256 numbered according to the EU index as in Kabat, and (iii) a human IgG4 core hinge region sequence comprising a substitution of the serine residue within the amino acid sequence CPSCP (SEQ ID NO:1) to proline also described as an S228P substitution according to the EU index as in Kabat;

wherein the in vivo half-life of the modified antibody, immunoglobulin construct or immunoglobulin IgG4 fusion protein is increased compared with the corresponding unmodified antibody, immunoglobulin construct or immunoglobulin IgG4 fusion protein.

Throughout the specification, the numbering of residues in an immunoglobulin heavy chain is that of the EU index or numbering system of Kabat (Kabat et al., Sequences of Proteins of Immunological Interest 5$^{th}$ Ed., Washington D.C. United States Department of Health and Human Services, 1991, National Institutes of Health, Bethesda. The "EU index as Kabat" refers to the numbering of the human IgG1 EU antibody (Edelman et al., *Proc. Natl. Acad. USA*, 63, 78-85, 1969). The amino acid sequences of IgG2, IgG3 and IgG4 isotypes are aligned with the IgG1 sequence by placing the first and last cysteine residues of the respective hinge regions, which form the inter-heavy chain S—S bonds, in the same positions.

Amino acid residues 251-256 according to the EU index as in Kabat are located within the immunoglobulin heavy chain CH2 domain of the Fc region. These residues have been implicated in binding of the Fc region to the FcRn and hence are implicated in altering antibody half-life.

In another example, the invention provides an isolated immunoglobulin construct with increased in vivo half-life, comprising:

(i) an antibody fragment;

(ii) a human IgG4 CH2 domain modified relative to a corresponding unmodified CH2 domain to comprise substitutions at one or more of amino acid residues 251-256 numbered according to the EU index as in Kabat, and (iii) a human IgG4 core hinge region sequence comprising a substitution of the serine residue within the amino acid sequence CPSCP (SEQ ID NO:1) to proline also described as an S228P substitution according to the EU index as in Kabat;

wherein the in vivo half-life of the modified immunoglobulin construct is increased compared with the corresponding unmodified immunoglobulin construct.

In one embodiment, the isolated immunoglobulin construct comprises a human IgG4 Fc region or FcRn binding domain thereof.

Preferably, the isolated immunoglobulin construct comprises substitutions M252Y, S254T and T256E numbered according to the EU index as in Kabat.

Specific antibody fragments include, but are not limited to (i) an Fab fragment (ii) an Fd fragment, (iii) an Fv fragment, (iv) a dAb fragment, (v) isolated CDR regions, (vi) F(ab')2 fragments, (vii) single chain Fv molecules (scFv), (viii) bispecific single chain Fv, and (ix) diabody (x) triabody and (xi) tetrabody.

The invention also provides immunoglobulin IgG4 fusion proteins with increased in vivo half-life comprising a bioactive molecule recombinantly fused or chemically conjugated or engineered to contain (i) a human IgG4 Fc region or the FcRn binding domain thereof modified relative to a corresponding unmodified IgG4 Fc region or FcRn binding domain thereof to comprise substitutions M252Y, S254T and T256E numbered according to EU index as in Kabat, and (ii) a human IgG4 comprising the amino acid substitution S228P in the core hinge region sequence according to the EU index as in Kabat.

The bioactive molecule may include protein or non-protein agents or non-immunoglobulin proteins.

In one embodiment, the bioactive molecule is a polypeptide.

In another example, the present invention provides an immunoglobulin IgG4 fusion protein with increased in vivo half-life, comprising:

(i) a bioactive molecule;

(ii) a human IgG4 CH2 domain modified relative to an IgG4 CH2 domain to comprise substitutions at one or more of amino acid residues 251-256 numbered according to the EU index as in Kabat, and (iii) a human IgG4 core hinge region sequence comprising a substitution of the serine residue within the amino acid sequence CPSCP (SEQ ID NO:1) to proline also described as an S228P substitution according to the EU index as in Kabat;

wherein the in vivo half-life of the modified immunoglobulin IgG4 fusion protein is increased compared with the corresponding unmodified immunoglobulin IgG4 fusion protein.

Preferably, the isolated immunoglobulin IgG4 fusion protein comprises a human IgG4 Fc region or FcRn binding domain thereof.

Preferably, the isolated immunoglobulin IgG4 fusion protein comprises substitutions M252Y, S254T and T256E numbered according to the EU index as in Kabat.

The human IgG4 core hinge region sequence according to the invention preferably comprises an S228P substitution according to the EU index as in Kabat. This substitution has also been referred to as S241P according to Kabat et al (1987 Sequences of proteins of immunological interest. United States Department of Health and Human Services, Washington D.C.). The substitution has the effect of making the sequence of the core of the hinge region the same as that of a wild-type IgG1 or IgG2 isotype antibody. With respect to the IgG4 isotype antibody, it results in the production of the homogenous form of the IgG4 antibody and hence abrogates the dissociation and reassociation of the heavy chains which often leads to the production of heterodimeric IgG4 antibodies.

The antibody, immunoglobulin construct or immunoglobulin IgG4 fusion molecule of the invention comprises a human IgG4 Fc region or FcRn binding domain thereof comprising a substitution at one or more of amino acid residues 252, 254 and 256 according to the EU index as in Kabat. In certain examples, the antibody, immunoglobulin construct or immunoglobulin IgG4 fusion protein according to the invention comprises a single substitution of any one of amino acid residues 252, 254 or 256 of the Fc region. In other examples, the antibody, immunoglobulin construct or immunoglobulin IgG4 fusion protein comprises substitutions of residues 252 and 254, or residues 254 and 256 or residues 252 and 256 of the Fc region. In a particular example, the antibody, immunoglobulin construct or immunoglobulin IgG4 fusion protein comprises substitutions at each of residues 252, 254 and 256 of the human IgG4 Fc region sequence.

In particular examples of the invention, residue 252 is substituted with tyrosine, phenylalanine, serine, tryptophan or threonine, residue 254 is substituted with threonine or serine, and residue 256 is substituted with serine, arginine, glutamine, glutamic acid, aspartic acid, alanine, asparagine or threonine. In a particular example, residue 252 is substituted with tyrosine (M252Y), residue 254 is substituted with threonine (S254T) and residue 256 is substituted with glutamic acid (T256E). These substitutions are referred to collectively as the "YTE modification".

In another embodiment, the antibody or immunoglobulin construct according to the invention may be further recombinantly fused, chemically conjugated or engineered to contain to a moiety. The moiety according to the invention may be selected from, but not limited to a therapeutic agent which is directly or indirectly bound to the antibody, a cytotoxin, a radioisotope, an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

In one example, the antibody modified according to the present invention is an antibody that specifically binds to human IL-5. In another example, the antibody modified according to the present invention is an antibody that specifically binds to human CD33.

Accordingly, in one example, the present invention also provides an isolated antibody that specifically binds to IL-5 comprising:

(i) a human IgG4 Fc region or the FcRn binding domain thereof modified relative to a corresponding unmodified human IgG4 Fc region or FcRn binding domain thereof to comprise amino acid substitutions M252Y, S254T and T256E numbered according to the EU index as in Kabat, and (ii) a human IgG4 core hinge region sequence comprising the amino acid substitution S228P according to the EU index as in Kabat, wherein the in vivo half-life of the modified antibody is increased compared with the half-life of the corresponding unmodified antibody.

In a particular example, the corresponding unmodified anti-IL-5 antibody is hu39D10.

In another embodiment, the Fab sequence of the isolated antibody may correspond to the light and heavy chain variable region sequence of mepolizumab.

In another example, the present invention provides an antibody that specifically binds to IL-5, the antibody comprising a constant heavy chain sequence set forth in SEQ ID NO: 6 and a heavy chain variable region sequence set forth in SEQ ID NO:7. In another example, the antibody that specifically binds to IL-5, further comprises a light chain comprising the variable and constant region sequences set forth in SEQ ID NO:8.

In another example, the present invention provides an isolated antibody that specifically binds to CD33 comprising:

(i) a human IgG4 Fc region or the FcRn binding domain thereof modified relative to a corresponding unmodified human IgG4 Fc region or FcRn binding domain thereof to comprise amino acid substitutions M252Y, S254T and T256E numbered according to the EU index as in Kabat, and (ii) a human IgG4 core hinge region sequence comprising the amino acid substitution S228P according to the EU index as in Kabat, wherein the in vivo half-life of the modified antibody is increased compared with the half-life of the corresponding unmodified antibody.

In a particular example, the anti-CD33 antibody modified according to the invention is the antibody huMab195.

In another example, the present invention provides an antibody that specifically binds to CD33, the antibody comprising a heavy chain sequence set forth in SEQ ID NO:11 and a light chain sequence set forth in SEQ ID NO:12.

The present invention also provides for the use of an isolated antibody, immunoglobulin construct or immunoglobulin IgG4 fusion protein with increased in vivo half live, comprising:

(i) a human IgG4 Fc region or the FcRn binding domain thereof modified relative to a corresponding unmodified IgG4 Fc region or unmodified FcRn binding domain thereof to comprise substitutions at one or more amino acid residues 251-256 numbered according to the EU index as in Kabat, and (ii) a human IgG4 core hinge region sequence comprising a substitution of the serine residue within the amino acid sequence CPSCP to proline (SEQ ID NO:1) also described as an S228P substitution according to the EU index as in Kabat;

in medicine.

Preferably, the isolated antibody, immunoglobulin construct or immunoglobulin IgG4 fusion protein comprises substitutions M252Y, S254T and T256E numbered according to the EU index as in Kabat.

The present invention also provides use of an isolated antibody, immunoglobulin construct or immunoglobulin IgG4 fusion protein modified according to the invention in the manufacture of a medicament for treating or preventing a disorder.

The invention provides use of an isolated antibody, immunoglobulin construct or immunoglobulin IgG4 fusion protein with increased in vivo half-life comprising:

(i) a human IgG4 Fc region or the FcRn binding domain thereof modified relative to a corresponding unmodified human IgG4 Fc region or FcRn binding domain thereof to comprise amino acid substitutions M252Y, S254T and T256E numbered according to the EU index as in Kabat, and (ii) a human IgG4 core hinge region sequence comprising the amino acid substitution S228P according to the EU index as in Kabat, in the manufacture of a medicament for treating or preventing a disorder in a subject.

The present invention also provides a method of treating or preventing a disorder in a subject characterised by excess eosinophil production comprising administering a modified anti-IL-5 antibody of the invention.

The present invention also provides a method of treating a disorder in a subject characterised by excess eosinophil production, comprising administering to the subject an isolated antibody that specifically binds IL-5 which comprises:

(i) a human IgG4 Fc region or the FcRn binding domain thereof modified relative to a corresponding unmodified IgG4 Fc region or unmodified FcRn binding domain thereof to comprise substitutions M252Y, S254T and T256E numbered according to the EU index as in Kabat, and (ii) a human IgG4 core hinge region sequence comprising the amino acid substitution S228P according to the EU index as in Kabat, wherein the in vivo half-life of the modified antibody is elevated compared with the half-life of the corresponding unmodified antibody.

The present invention also extends to the use of such modified antibodies in treating or preventing a disorder in a subject characterised by excess eosinophil production and to the use of the modified antibodies in the manufacture of a medicament for treating or preventing a disorder characterised by excess eosinophil production.

In one example, the invention provides use of an isolated antibody with increased in vivo half-life that specifically binds to IL-5, comprising:

(i) a human IgG4 Fc region or the FcRn binding domain thereof modified relative to a corresponding unmodified human IgG4 Fc region or FcRn binding domain thereof to comprise amino acid substitutions M252Y, S254T and T256E numbered according to the EU index as in Kabat, and (ii) a human IgG4 core hinge region sequence comprising the amino acid substitution S228P according to the EU index as in Kabat, in the manufacture of a medicament for treating or preventing a disorder characterised by excess eosinophil production in a subject.

In one example, the disorder is characterised by excess eosinophil production (eosinophilia).

A disorder characterised by excess eosinophil production may be selected from the group consisting of atopic asthma, atopic dermatitis, allergic rhinitis, non-allergic rhinitis, asthma, sever asthma, chronic eosinophilic pneumonia, allergic bronchopulmonary aspergillosis, celiac disease, Churg-Strauss syndrome, eosinophilic myalgia syndrome, hypereosinophilic syndrome, oedematous reactions including episodic angiodema, helminth infections, onchocercal dermatitis, eosinophilic oesophagitis, eosinophilic gastritis, eosinophilic gastroenteritis, eosinophilic enteritis, eosinophilic colitis, nasal micropolyposis, nasal polyposis, aspirin intolerance asthma, obstructive sleep apnea, chronic asthma, Crohn's disease, scleroderma and endomyocardial fibrosis.

In another example, the disorder is autoimmune disease.

It will also be appreciated that the modified anti-IL-5 antibody according to the invention can be used in methods of prophylaxis or diagnosis relating to a disorder characterised by excess eosinophil production.

The invention also provides a method of treating a cancer disorder in a subject, comprising administering a modified anti-CD33 antibody according to the invention to the subject.

The present invention also provides a method of treating a cancer disorder in a subject, comprising administering to the subject an isolated antibody that specifically binds CD33, comprising:

(i) a human IgG4 Fc region or the FcRn binding domain thereof modified relative to a corresponding unmodified IgG4 Fc region or unmodified FcRn binding domain thereof to comprise substitutions M252Y, S254T and T256E numbered according to the EU index as in Kabat, and (ii) a human IgG4 core hinge region sequence comprising the amino acid substitution S228P according to the EU index as in Kabat, wherein the in vivo half-life of the modified antibody is increased compared with the half-life of the corresponding unmodified antibody.

The present invention also extends to the use of such modified antibodies in treating or preventing a cancer disorder and to the use of the modified antibodies in the manufacture of a medicament for treating or preventing a cancer disorder.

In a particular example, the cancer disorder is acute myeloid leukemia.

In another example, the invention provides use of an isolated antibody with increased in vivo half-life that specifically binds to CD33, comprising:

(i) a human IgG4 Fc region or the FcRn binding domain thereof modified relative to a corresponding unmodified human IgG4 Fc region or unmodified FcRn binding domain thereof to comprise amino acid substitutions M252Y, S254T and T256E numbered according to the EU index as in Kabat; and (ii) a human IgG4 core hinge region sequence comprising the amino acid substitution S228P according to the EU index as in Kabat;

in the manufacture of a medicament for treating or preventing a cancer disorder in a subject.

In a particular example, the cancer disorder is acute myeloid leukemia.

The present invention also provides a method for increasing the in vivo half-life of a human or humanised IgG4 isotype antibody or immunoglobulin construct comprising an IgG4 Fc region or FcRn binding domain thereof and IgG4 hinge region, the method comprising:

(i) introducing amino acid substitutions M252Y, S254T and T256E numbered according to the EU index as in Kabat into the Fc region sequence or FcRn binding domain thereof, and (ii) introducing the amino acid substitution S228P according to the EU index as in Kabat into the core hinge region sequence.

In a particular example, the above method can be used to increase the half-life of an anti-IL-5 antibody, in particular hu39D10.

In a further particular example, the above method can be used to increase the half-life of an anti-CD33 antibody.

The present invention also provides a method for increasing the in vivo half life of an immunoglobulin IgG4 fusion protein comprising an IgG4 Fc region or FcRn binding domain thereof and IgG4 hinge region, the method comprising:

(i) introducing into a human IgG4 Fc region or FcRn binding domain thereof amino acid substitutions M252Y, S254T and T256E numbered according to the EU index as in Kabat; and (ii) introducing the amino acid substitution S228P according to the EU index as in Kabat into a human IgG4 core hinge region sequence.

The invention also provides a method for increasing the in vivo half life of a protein by engineering it as a fusion protein comprising SEQ ID NO:14.

The invention also provides a fusion protein comprising SEQ ID NO:14.

In one example the fusion protein further comprises a single lysine attached immediately C-terminal to SEQ ID NO:14.

The invention also provides a method for reducing effector function of a non IgG4 antibody, the method comprising:

(i) replacing the heavy chain constant region of the non-IgG4 antibody with a human IgG4 constant region or FcRn-binding domain thereof, modified to comprise amino acid substitutions M252Y, S254T and T256E numbered according to the EU index as in Kabat; and (ii) replacing the hinge region of the non-IgG4 antibody with an IgG4 hinge region having the amino acid substitution S228P according to the EU index as in Kabat.

The invention also provides a method for increasing the in vivo half-life of a non-human IgG4 antibody, the method comprising:

(i) replacing the heavy chain constant region of the non-human-IgG4 antibody with a human IgG4 constant region or FcRn-binding domain thereof, modified to comprise amino acid substitutions M252Y, S254T and T256E numbered according to the EU index as in Kabat; and (ii) replacing the hinge region of the non-human IgG4 antibody with an IgG4 hinge region having the amino acid substitution S228P according to the EU index as in Kabat.

The present invention also provides a nucleic acid encoding an antibody, immunoglobulin construct or immunoglobulin IgG4 fusion protein as described herein according to any embodiment.

The present invention also provides a transformed cell expressing an antibody, immunoglobulin construct or immunoglobulin IgG4 fusion protein as described herein according to any embodiment.

The present invention also provides a transformed cell comprising a nucleic acid encoding an antibody, immunoglobulin construct or immunoglobulin IgG4 fusion protein as described herein.

In another embodiment, the invention provides a pharmaceutical composition comprising the isolated antibody, immunoglobulin construct or immunoglobulin IgG4 fusion protein according to the invention, together with a pharmaceutically acceptable excipient. Preferably, the composition comprises a therapeutically effective amount or the antibody, immunoglobulin construct or immunoglobulin IgG4 fusion protein.

DESCRIPTION OF THE FIGURES

FIG. 1A shows the sequence of the relizumab heavy chain, including the variable domain and the IgG4 constant domain, sequences of the constant domain (native IgG4 isotype) or the IgG4 constant domain with the S228P mutation, or the "YTE" mutations. FIG. 1B shows the sequence o the IgG4 constant domain with a combination of the S228P and the YTE mutations and, the sequence of the hu39D10 heavy chain variable domain and the hu39D10 light chain.

FIG. 2 shows the sequence of the human FcRn extracellular domain.

FIG. 3 shows the sequence of the mature portion of human beta2 microglobulin.

FIG. 6 shows the sequence of the CD33 antibody huMab195 in which the Fc domain is an IgG4 isotype containing the S228P and TYE modifications; also shown is the light chain of huMab195.

FIG. 7 shows the sequence of the human CD33 extracellular domain-Fc fusion protein.

FIG. 9 shows the sequence of hinge-Fc portion of native human IgG4 heavy chain and the sequence of hinge-Fc portion of human IgG4 heavy chain with S228P and YTE mutations and lacking the C-terminal lysine.

DETAILED DESCRIPTION OF THE INVENTION

General

Figure 4:
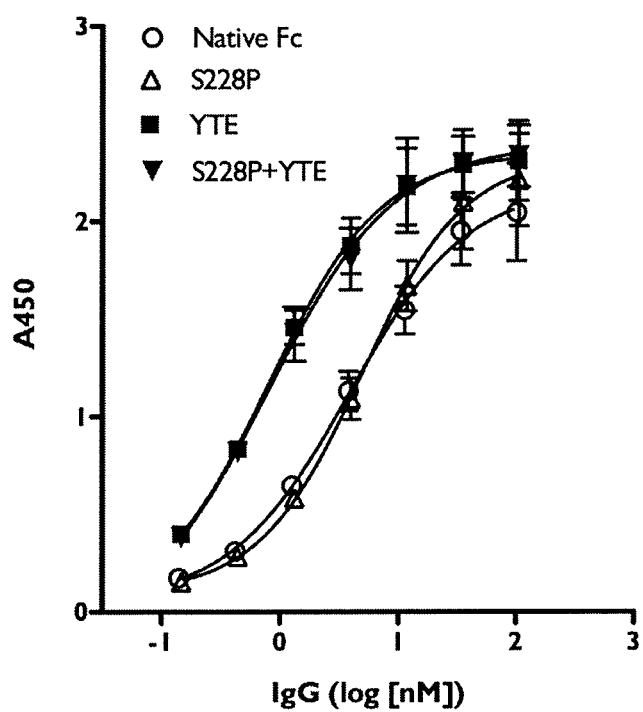
FIG. 4 shows an ELISA-based assay to measure the affinity of human FcRn for hu39D10 containing a native IgG4 Fc domain, or one that carries the S228P mutation, the YTE mutations, or both the S228P and the YTE mutations.

The term "and/or", e.g., "X and/or Y" shall be understood to mean either "X and Y" or "X or Y" and shall be taken to provide explicit support for both meanings or for either meaning.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the disclosure is to be applied mutatis mutandis to each and every other embodiment unless specifically stated otherwise.

Those skilled in the art will appreciate that the disclosure herein is susceptible to variations and modifications other than those specifically described. It is to be understood that the disclosure encompasses all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

The compositions of matter and methods described herein are produced or performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, J. eds.), vol. 2, pp. 1-284, Academic Press, New York. 12. Wunsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Definitions

As used herein the term "corresponding" unmodified antibody means an antibody of the same sequence as the modified antibody but without the changes to the amino acid sequence described herein, in particular the Fc and the hinge region.

The term "epitope" is intended to refer to the part of an antigenic molecule to which an antibody is produced and to which the antibody will bind. The term "epitope," as used herein, refers to (a) portion(s) of a peptide having antigenic or immunogenic activity in an animal, preferably a vertebrate, more preferably a mammal, and most preferably in a human or a transgenic animal expressing relevant components of the human immune system. Epitopes may comprise proteins, protein fragments, peptides, carbohydrates, lipids, and other molecules, but for the purposes of the present invention are most commonly short oligopeptides. The term "epitope" is intended to encompass an "immunogenic epitope", an "antigenic epitope", or "antigen epitope".

The term "antibody" as used herein refers to a molecule that is capable of binding to a target through at least one epitope recognition site, located in the variable region of the immunoglobulin molecule. The terms immunoglobulin and antibody may be used interchangeably throughout the specification. The immunoglobulin or antibody molecule includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, Superhumanized® antibodies, half antibodies, bispecific antibodies). An antibody generally comprises constant domains, which can be arranged into a constant region or constant fragment or fragment crystallisable (Fc). Exemplary forms of antibodies comprise a four-chain structure as their basic unit. Full-length antibodies comprise two heavy chains (~50-70 kD) covalently linked and two light chains (~23 kD each). Each heavy and light chain comprises variable regions and constant domains. A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Unmodified antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass.

The term "immunoglobulin construct" as used herein refers to a construct comprising at least a CH2 heavy chain constant domain and hinge region from a primate or human IgG4 antibody. Preferably, the term is intended to refer to a construct comprising at least light and heavy chain constant domains and hinge region from a primate or human IgG4 antibody.

The term "constant region" or "constant fragment" refers to the portion of an immunoglobulin or antibody molecule having a core conserved amino acid sequence relative to the other portion of the immunoglobulin or antibody, termed the variable region, which contains the antigen binding site. In the heavy chain, the constant region contains the CH1, CH2 and CH3 domains.

The term "Fc region" as used herein refers to the portion of an antibody or immunoglobulin molecule that correlates to a crystallisable fragment obtained by papain digestion of an IgG molecule. The Fc region consists of the C-terminal region of an IgG heavy chain-made up of the C-terminal approximately half of the two heavy chains of an IgG molecule that are linked by disulfide bonds. Although boundaries may vary slightly (in some cases it includes part of the hinge), as numbered according to the EU index of Kabat, the Fc region extends from amino acid 231 to amino acid 447. The Fc region of an IgG comprises two constant domains, CH2 and CH3. The CH2 domain of a human IgG Fc region usually extends from amino acid 231 to amino acid 341 according to the EU index of Kabat. The CH3 domain of a human IgG Fc region usually extends from amino acids 342 to 447 according to the EU index of Kabat. The Fc region has no antigen binding activity but contains the carbohydrate moiety and the binding site for the Fc receptor, including the neonatal Fc receptor (FcRn).

The term "FcRn binding domain thereof" as used herein refers to a portion of the Fc region which is capable of binding to FcRn. In the present context, it is also intended to refer to a fragment of the Fc region sequence including at least the CH2 domain.

The term "FcRn receptor" as used herein refers to an Fc receptor ("n" indicating neonatal) which is involved in transfer of maternal IgGs to a foetus through the human or primate placenta and to a neonate from the colostrum through the small intestine. The FcRn is also involved in the maintenance of constant serum IgG levels by binding the IgG molecules and recycling them into the serum. The binding of FcRn to IgG molecules is strictly pH dependent with optimum binding at pH 6.0. The FcRn is typically complexed with beta2 microglobulin.

The "hinge region" as used herein refers to a proline-rich portion of an immunoglobulin heavy chain between the Fc and Fab regions that confers mobility on the two Fab arms of the antibody molecule. It is located between the first and second constant domains of the heavy chain. The hinge region includes cysteine residues which are involved in inter-heavy chain disulfide bonds. It is generally defined as stretching from Glu216 to Pro230 of human IgG1 according to the EU numbering system of Kabat (or Glu226 to Pro243 according to the numbering system of Kabat). Hinge regions of other IgG isotypes may be aligned with the IgG1 sequence by placing the first and last cysteine residues forming inter-heavy chain disulphide (S—S) bonds in the same positions (see for example WO 2010/080538). The hinge region includes cysteine residues which are involved in inter-heavy chain disulfide bonds.

The term "core hinge region sequence" as used herein is intended to refer to the amino acid sequence CPSCP (SEQ ID NO:1) present in IgG4 and extending from amino acid 226 to 230 according to the EU index of Kabat (often referred to as the lower hinge). The core hinge region is distinguished from the upper hinge region which in a human IgG4 is the sequence ESKYGPP.

The term "variable region" as used herein "refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

The term "Fab" as used herein is intended to refer to a region of an antibody composed of one constant and one variable domain of each of the heavy and the light chains (monovalent antigen-binding fragment), but wherein the heavy chain is truncated such that it lacks the CH2 and CH3 domain (ie VH, CH1, VL, and CL), and may also lack some or all of the hinge region. It can be produced by digestion of a whole antibody with the enzyme papain. Fab may refer to this region in isolation, or this region in the context of a full length antibody, immunoglobulin construct or Fab fusion protein.

The term Fab' as used herein can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner.

By "scFv" it is meant an antibody fragment comprising the VH and VL domains of an antibody, wherein these domains are present in a single polypeptide chain. See, for example, U.S. Pat. Nos. 4,946,778, 5,260,203, 5,455,030, and 5,856,456. Generally, the Fv polypeptide further comprises a polypeptide linker between the $V_H$ and VL domains that enables the scFv to form the desired structure for antigen-binding. For a review of scFv see Pluckthun (1994) The Pharmacology of Monoclonal Antibodies vol 113 ed. Rosenburg and Moore (Springer-Verlag, New York) pp 269-315. The VH and VL domain complex of Fv fragments may also be stabilized by a disulfide bond (U.S. Pat. No. 5,747,654).

By "no or minimal effector function" it is meant that certain activities normally attributable to IgG1 type antibodies such as complement fixation or stimulation of antibody-dependent cell-mediated cytotoxicity (ADCC) are reduced or eliminated.

The term "isolated" as used herein refers to an antibody, immunoglobulin construct or immunoglobulin IgG4 fusion protein removed from its native environment. Thus, an antibody, immunoglobulin construct or fusion protein produced by a recombinant host is considered isolated for the purposes of the present invention. Preferably, the isolated antibody, immunoglobulin construct or immunoglobulin IgG4 fusion protein is substantially purified.

By "substantially purified" is meant that the antibody, immunoglobulin construct or immunoglobulin IgG4 fusion protein is substantially free of cellular material or other contaminating proteins from the cell or tissue source from which it is derived, or is substantially free from chemical precursors or other chemicals when chemically synthesised. The language includes preparations of an antibody, immunoglobulin construct or fusion protein which is separated from cellular components of the cells from which it is isolated or recombinantly produced. Thus, an antibody, immunoglobulin construct or immunoglobulin IgG4 fusion protein that is substantially free of cellular material includes preparations having less than about 30%, 20%, 10% or 5% (by dry weight) of contaminating protein and culture medium.

The term "immunoglobulin IgG4 fusion protein" refers to a bioactive molecule which is linked or attached to a modified human IgG4 hinge region and modified human IgG4 Fc region and/or FcRn binding domain thereof. Fusion proteins are discussed in further detail later.

The term "in vivo half-life" as used herein refers to a circulating half-life of a particular antibody, immunoglobulin construct or immunoglobulin IgG4 fusion protein containing an Fc region and/or FcRn binding domain thereof in the circulation of a given animal and is represented by a time required for half the quantity administered in the animal to be cleared from the circulation. When a clearance curve of a given antibody, immunoglobulin construct or immunoglobulin IgG4 fusion protein according to the invention is constructed as a function of time the curve is usually biphasic with a rapid alpha phase which represents an equilibration of the injected IgG molecules between the intra and extra vascular space and which is, in part determined by the size of the molecules, and a longer beta phase which represents the catabolism of the IgG molecules in the intravascular space. The term "in vivo half-life" practically corresponds to the half-life of the modified or unmodified IgG4 immunoglobulins or fusion proteins in the beta phase.

The term "increased in vivo half life" as used herein means that the antibody, immunoglobulin construct or immunoglobulin IgG4 fusion protein modified according to the invention has a greater persistence in the serum or plasma and/or takes a greater period of time to reduce to half the maximal measured serum or plasma concentration relative to the same antibody, immunoglobulin construct or immunoglobulin IgG4 fusion protein that does not contain the same substitutions.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody variable region. Similarly, if a nucleic acid encoding the protein is isolated and expressed using recombinant means, the resulting protein is a recombinant protein comprising an antibody antigen binding domain. A term recombinant also encompasses an antibody, immunoglobulin or fusion protein expressed by artificial recombinant means when it is within a cell, tissue or subject, e.g., in which it is expressed.

The term "specifically binds" refers to a molecule (eg. antibody, immunoglobulin construct or immunoglobulin IgG4 fusion protein) that specifically or preferentially binds to an antigen (e.g., eptiope or immune complex) and does not specifically bind to (i.e. cross-react with) antigens, such as, for example, other structurally or functionally related proteins, or proteins with sequence homology. A molecule that specifically binds to an antigen may bind to other peptides or polypeptides with lower affinity as determined by, e.g., immunoassays, BIAcore, or other assays known in the art. Preferably, molecules that specifically bind an antigen do not cross-react with other proteins. Molecules that specifically bind an antigen can be identified, for example, by immunoassays, BIAcore, or other techniques known to those of skill in the art. By way of non-limiting example, an antibody may be considered to bind to an antigen preferentially if it binds said antigen with dissociation constant ($K_D$) that is less than the antibody's $K_D$ for another antigen. In another non-limiting example, an antibody may be considered to bind a first antigen preferentially if it binds said first antigen with an affinity that is at least one order of magnitude less than the antibody's $K_D$ for the second antigen. In another non-limiting embodiment, an antibody may be considered to bind a first antigen preferentially if it binds said first antigen with an affinity that is at least two orders of magnitude less than the antibody's $K_D$ for the second antigen.

The term "treating" or "treat" as used herein refers to administering a "therapeutically effective amount" of the antibody, immunoglobulin construct or fusion protein according to the invention sufficient to reduce or eliminate at least one symptom of a specified disease or condition.

The term "prevent" or "preventing" as used herein refers to administration of a therapeutically effective amount of an antibody, immunoglobulin construct or immunoglobulin IgG4 fusion protein sufficient to stop or hinder the development of a specified disorder or condition.

As used herein, the term "therapeutically effective amount" shall be taken to mean a sufficient quantity of an antibody, immunoglobulin construct or immunoglobulin IgG4 fusion protein to reduce or inhibit one or more symptoms of a clinical disease to a level that is below that observed and accepted as clinically diagnostic or clinically characteristic of that disease. The skilled artisan will be aware that such an amount will vary depending on, for example, the specific antibody(ies), immunoglobulin construct(s) and/or immunoglobulin IgG4 fusion protein(s) administered and/or the particular subject and/or the type or severity or level of disease. Accordingly, this term is not to be construed to limit the invention to a specific quantity, e.g., weight or amount rather the present invention encompasses any amount of the antibody(ies), immunoglobulin construct(s) and/or immunoglobulin IgG4 fusion protein(s) sufficient to achieve the stated result in a subject.

The term "pharmaceutically acceptable" as used herein means approved by a regulatory agency of the federal or a state government or listed in the US Pharmacopeia or other generally recognised pharmacopeia for use in humans.

As used herein, the term "subject" shall be taken to mean a human or non-human primate, or non-primate mammal with a human FcRn.

Amino Acid Substitutions

Methods of substituting amino acids are known in the art. For example, amino acid substitutions can be made by site-directed mutagenesis (for example, Zoller and Smith Nucl. Acids Res. 10:6487 (1982)). Mutagenesis can be performed by synthesising an oligonucleotide having one or more modifications within the sequence of the constant domain of an antibody to be modified. Site-specific mutagenesis allows the production of mutants through the use of specific oligonucleotide sequences which encode the DNA sequence of the desired mutation, as well as a sufficient number of adjacent oligonucleotides to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generate a library of mutants.

The technique of site-specific mutagenesis is well known in the art, (see, e.g., Kunkel et al., *Methods Enzymol.,* 154:367-82, 1987). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage. Site directed mutagenesis has also been used to identify amino acid residues that influence plasma clearance of murine IgG1 hinge-Fc fragments as described in Kim Jin-Kyoo et al., (1994) Eur. J. Immunol. 24:542-548).

Alternatively, the use of PCR with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.,* 18(6):1656, 1987, and Upender et al., *Biotechniques,* 18(1):29-30, 32, 1995, for PCR-mediated mutagenesis procedures. PCR employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques,* 16(3):410-2, 1994).

Other methods known to those of skill in art of producing sequence variants of the Fc region of an antibody or an FcRn binding domain thereof can be used. For example, recombinant vectors encoding the amino acid sequence of the constant domain of an antibody or a fragment thereof may be treated with mutagenic agents, such as hydroxylamine, to obtain sequence variants.

Mutants that result in increased affinity for FcRn and increased in vivo half-life can be screened using routine assays such as those described later. Exemplary amino acid substitutions include T250Q and/or M428L or T252A, T254S and T266F or M252Y, S254T and T256E or H433K and N434F according to the EU Kabat numbering system. Additional or alternative amino acid substitutions are described, for example, in US20070135620 or US7083784.

Antibodies of the Invention

The antibody or immunoglobulin according to the invention includes any immunoglobulin molecule or antibody that binds, (as determined by immunoassays known in the art for assaying specific antigen-antibody binding) an antigen and contains an Fc region or FcRn binding domain. The antibodies may be polyclonal, monoclonal or monospecific, bi-specific (in the context of multimeric forms of the antibody), human, humanised, chimeric, Superhumanised®, primatised or deimmunised. In another example, the antibodies of the present invention may be monospecific, (or bispecific, trispecific or of greater multispecificity if present in multimeric form).

In particular, the antibody is a monospecific tetramer.

The antibody (and other immunoglobulin construct or fusion protein described herein) may be from any animal origin. Preferably, the antibody is human or humanised. As used herein the term "human" antibody include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598.

The antibody(ies) of the invention comprise a stabilized IgG4 hinge region. The term "stabilized IgG4 hinge region" will be understood to mean an IgG4 hinge region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

The stabilized IgG4 hinge region comprises a serine to proline substitution at position 228 according to the EU numbering system of Kabat (Kabat et al., Sequences of Proteins of Immunological Interest Washington D.C. United States Department of Health and Human Services, 2001 and Edelman et al., *Proc. Natl. Acad. USA,* 63, 78-85, 1969), which corresponds to a serine to proline substitution at position 241 according to the numbering system of Kabat (Kabat et al., Sequences of Proteins of Immunological Interest Washington D.C. United States Department of Health and Human Services, 1987 and/or 1991). For the avoidance of doubt, this refers to the serine in the center of the IgG4 hinge region sequence CPSCP (SEQ ID NO:1). Following substitution of the serine for proline, the IgG4 hinge region comprises a sequence CPPCP. In this regard, the skilled person will be aware that the "hinge region" is a proline-rich portion of an antibody heavy chain constant region that links the Fc and Fab regions that confers mobility on the two Fab arms of an antibody.

In one example, the antibody of the invention may be in a multimeric form. For example, the antibody may take the form of an antibody dimer, trimer, or higher-order multimer of monomeric immunoglobulin molecules. Dimers of whole immunoglobulin molecules or of F(ab')$_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known to one of ordinary skill in the art. For example, some percentage of purified antibody preparations spontaneously form protein aggregates containing antibody homodimers, and other higher-order antibody multimers. Alternatively, antibody homodimers may be formed through chemical linkage techniques known in the art. As a non-limiting example, heterobifunctional crosslinking agents including, but not limited to, SMCC [succinimidyl 4-(maleimidomethyl)cyclohexane-I-carboxylate] and SATA [N-succinimidyl S-acethylthio-acetate] (available, for example, from Pierce Biotechnology, Inc. (Rockford, 111.)) can be used to form antibody multimers. An exemplary protocol for the formation of antibody homodimers is given in Ghetie M A et al. Antibody homodimers can be converted to F(ab')$_2$ homodimers through digestion with pepsin. Another way to form antibody homodimers is through the use of the autophilic TI 5 peptide described in Zhao Y & Kohler H J. Immunother (1997) 25(5):396-404.

Alternatively, antibodies can be made to multimerize naturally or through recombinant DNA techniques. ScFv dimers can also be formed through recombinant techniques known in the art; an example of the construction of scFv dimers is given in Goel A et al. Cancer Research 60(24): 6964-6971. Antibody multimers may be purified by any suitable method known in the art, e.g. size exclusion chromatography.

Antibody Derivatives

The present invention also provides antibodies that comprise, or alternatively consist of, variants (including derivatives) of the antibody molecules (e.g. the V$_H$ domains and/or V$_L$ domains) described herein, which antibodies specifically bind antigen peptides (for example, the IL-5 antigen or the CD33 antigen). Standard techniques known to those of skill in the art can be used to introduce mutations in the nucleotide sequence encoding a molecule of the invention, including for example, site-directed mutagenesis and PCR-mediated mutagenesis which result in amino acid substitutions.

Antibody derivatives according to the invention also encompass conservative amino acid substitutions into the immunoglobulin V$_L$ and/or V$_H$ region. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind antigen peptides of the invention (e.g. the ability to bind antigen peptides of the invention).

The term "conservative substitution" shall be taken to mean amino acid substitutions set forth in Table 1.

TABLE 1

Exemplary Substitutions

| Original residue | Exemplary substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro; ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

For example, it is possible to introduce mutations only in framework regions or only in CDR regions of an antibody molecule. Introduced mutations may be silent or neutral missense mutations, i.e. have no, or little, effect on the antibody's ability to bind antigen. These types of mutations may be useful to optimize codon usage, or improve antibody production from a cell line.

Alternatively, non-neutral missense mutations may alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to specifically bind antigen peptides of the invention) can be determined using techniques described herein or by routinely modifying techniques known in the art.

The antibodies of the invention include derivatives that are otherwise modified by covalent attachment of any type of molecule to the antibody such that covalent attachment does not prevent the antibody from binding antigen. For example, the antibody derivatives include antibodies that have been modified, for example, by glycosylation, acetylation, pegylation, phosphorylation, amidation, derivatisation by known protecting/blocking groups, proteolytic cleavage, linkage to a cellular ligand or other protein etc. Any of numerous chemical modifications may be carried out by techniques known in the art, including specific chemical cleavage, acetylation, formylation, metabolic synthesis of tunicamycin etc. Additionally, the derivative may contain one or more non-classical amino acids.

In addition, antibodies of the invention may be chemically synthesized. For example, a peptide corresponding to a portion of a protein can by synthesized by use of a peptide synthesizer. Furthermore, if desired, non-classical amino acids or chemical amino acid analogs can be introduced as substitutions and/or additional into the sequence of one, any, both, several or all of the polypeptides of the complex.

Non-classical amino acids include, but are not limited to, the D-isomers of the common amino acids, fluoro-amino acids, designer amino acids such as beta-methyl amino acids, C gamma-methyl amino acids, N gamma-methyl amino acids, and, and amino acid analogs in general.

The present invention also provides immunoconjugates comprising an antibody or immunoglobulin contract of the present invention conjugated to a distinct moiety e.g. a therapeutic agent which is directly or indirectly bound to the antibody. Examples of other moieties include, but are not limited to, a cytotoxin, a radioisotope (e.g., iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

A cytotoxin includes any agent that is detrimental to (e.g., kills) cells. For a description of these classes of drugs which are known in the art, and their mechanisms of action, see Goodman et al., Goodman and Gilman's The Pharmacological Basis of Therapeutics, 8th Ed., Macmillan Publishing Co., 1990. Additional techniques relevant to the preparation of antibody immunotoxins are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

A variety of radionuclides are available for the production of radioconjugated antibodies. Examples include, but are not limited to, $^{212}Bi$, $^{131}I$, $^{90}Y$ and $^{186}Re$.

Conjugates of the antibody and therapeutic agents are made using a variety of bifunctional protein-coupling agents such as, but not limited to, 4-(4'acetylphenoxy)butanoic acid (AcBut), 3-acetylphenyl acidic acid (AcPac), 4-mercapto-4-methyl-pentanoic acid (Amide), N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene), and derivatives thereof. For example, a ricin immunotoxin can be prepared as described by Vitetta et al. (1987). Carbon-14-labeled 1-isothiocyanatobenzyl-3-methyldiethylene triaminepentaacetic acid (MX-DTPA) is an exemplary chelating agent for conjugation of radionucleotide to the antibody (WO 94/11026).

Immunoglobulin Constructs of the Invention

As used herein, the term "immunoglobulin construct" is intended to refer to constructs in which an antigen binding antibody fragment is linked to a modified human IgG4 hinge region and modified human IgG4 Fc region or FcRn binding domain thereof according to the present invention.

Of particular interest are immunoglobulin constructs that comprise Fc regions, Fc fusions and the constant region of the heavy chain (CH1-hinge-CH2—CH3).

Specific antibody fragments include, but are not limited to (i) the Fab fragment consisting of VL, VH, CL and CH1 domains; (ii) the Fd fragment consisting of the VH and CH1 domains, (iii) the Fv fragment consisting of the VL and VH domains of a single antibody, (iv) the dAb fragment (Ward et al., (1989) Nature 341:544-546) which consists of single variable region (v) isolated CDR regions (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., (1988) Science 242:423-426, Huston et al., (1989) Proc Natl Acad Sci USA 85:5879-5883), (viii) bispecific single chain Fv (WO 03/11161), and (ix) diabodies and triabodies or tetrabodies (Tomlinson et al., (2000) Methods Enzymol 326:461-479; WO 94/13804; Hollinger et al., (1993) Proc Natl Acad Sci USA 90:6444-6448). The molecules may be stabilised by the incorporation of disulphide bridges linking the VH and VL domains (Reiter et al., (1996) nature Biotech 14:1239-1245).

It will be appreciated that the fragments described above (which do not contain a hinge region) may be joined to a hinge-Fc region where the hinge serves as a linker.

In another example, the antibody fragment may be a flex minibody consisting of scFV-CH3 and hinge region sequence (as described in Hu, Shi-zhen et al., (1996) Cancer Research 56:3055-3061).

Antibody Preparation

Antibodies can be prepared using a wide variety of techniques known in the art including the use of hybridoma, recombinant and phage display technologies or a combination thereof. For example monoclonal antibodies can be produced using hybridoma techniques including those known in the art and taught by e.g. Harlow et al., Antibodies: A laboratory Manual (Cold Spring Harbor Laboratory Press $2^{nd}$ Edn 1988).

The term "monoclonal antibody" as used herein is not limited to antibodies produced through hybridoma technology. The term refers to any antibody that is derived from a single clone, including any prokaryotic, eukaryotic, or phage clone and not the method by which it is produced.

Methods for producing and screening for specific antibodies using hybridoma technology are routine in the art. For example, mice can be immunised with an antigen of interest or a cell expressing such an antigen. Once an immune response is detected, the mouse spleen is harvested and splenocytes isolated. The splenocytes are then fused to myeloma cells. Hybridomas are selected and cloned by limiting dilution. The clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by routine techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

Antibodies can also be generated using various phage display methods. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labelled antigen or antigen bound or captured to a solid surface or bead. Phage used in these methods are typically filamentous phage, including fd and M13. The antigen binding domains are expressed as a recombinantly fused protein to either the phage gene III or gene VIII protein. Alternatively, the modified FcRn binding portion of immunoglobulins of the present invention can be also expressed in a phage display system. Examples of phage display methods that can be used to make the immunoglobulins, or fragments thereof, of the present invention include those disclosed in Brinkman et al., *J. Immunol. Methods*, 182:41-50, 1995; Ames et al., *J. Immunol. Methods*, 184: 177-186, 1995; Kettleborough et al., *Eur. J. Immunol.*, 24:952-958, 1994; Persic et al., *Gene*, 187:9-18, 1997; Burton et al., *Advances in Immunology*, 57:191-280, 1994; PCT application No. PCT/GB91/01134; PCT publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580, 717; 5,427,908; 5,750,753; 5,821,047; 5,571,698; 5,427, 908; 5,516,637; 5,780,225; 5,658,727; 5,733,743 and 5,969, 108.

After phage selection, the antibody coding regions from the phage can be isolated and used to generate whole antibodies, including human antibodies, or any other desired fragments, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques*, 12(6):864-869, 1992; and Sawai et al., AJRI, 34:26-34, 1995; and Better et al., *Science*, 240:1041-1043, 1988, examples of techniques which can be used to produce single-chain Fvs and antibodies include those described in U.S. Pat. Nos. 4,946,778 and 5,258,498; Huston et al., *Methods in Enzymology*, 203:46-88, 1991; Shu et al., *PNAS*, 90:7995-7999, 1993; and Skerra et al., *Science*, 240:1038-1040, 1988.

Recombinant Production of Antibodies, Immunoglobulin Constructs and Immunoglobulin IgG4 Fusion Proteins The antibodies, immunoglobulin constructs and immunoglobulin IgG4 fusion proteins of the present invention can be produced recombinantly. For example, DNA encoding an antibody, immunoglobulin construct or immunoglobulin IgG4 fusion protein of the invention is readily isolated and sequenced using conventional procedures (e.g., by using oligonucleotide probes that are capable of binding specifically to genes encoding the heavy and light chains of antibodies). A hybridoma cell serves as a preferred source of such DNA for antibodies. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al, *Curr. Opinion in Immunol.*, 5:256-262 (1993) and Pluckthun, *Immunol. Revs.*, 130:151-188 (1992). Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, Guide to Molecular Cloning Techniques, Methods in Enzymology volume 152 Academic Press, Inc., San Diego, Calif. (Berger); Sambrook et al. (1989) Molecular Cloning A Laboratory Manual (2nd ed.) Vol. 1 3, Cold Spring Harbor Laboratory, Cold Spring Harbor Press, N.Y., (Sambrook); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) Proc. Natl. Acad. Sci. USA 86: 10029 10033.

For recombinant production, the nucleic acid encoding the antibody, immunoglobulin construct or immunoglobulin IgG4 fusion protein is preferably isolated and inserted into a replicable vector for further cloning (amplification of the DNA) or for expression. DNA encoding the antibody or fusion protein is readily isolated or synthesized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, a sequence encoding an antibody of the present invention or fragment thereof (e.g., derived from the information provided herein), an enhancer element, a promoter, and a transcription termination sequence.

(i) Signal sequence component. The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, a factor leader, or acid phosphatase leader, the *C. albicans* glucoamylasc leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the antibody.

(ii) Promoter component. Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S. D.) sequence operably linked to the DNA encoding the antibody.

Promoters are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2). CMV, bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

(iii) Enhancer element component. Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) Nature 297: 17-18 on enhancing elements for activation of eukaryotic promoters. The enhancer may be spliced into the vector at a position 5' or 3' to the antibody-encoding sequence, but is preferably located at a site 5' from the promoter.

(iv) Transcription termination component. Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/1 1026 and the expression vector disclosed therein.

(v) Selection and transformation of host cells. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito),

*Aedes albopictus* (mosquito), *Drosophila melanogaster* (fruitfly), and *Bombyx mori* have been identified. A variety of viral strains for transfection are publicly available, e.g., the L-I variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CVI line transformed by SV40 (COS-7, ATCC CRL 1651); human embryonic kidney line (293 or 293 cells subcloned for growth in suspension culture, Graham et al. (1977) Gen Virol. 36:59); baby hamster kidney cells (BHK, ATCC CCL 10); Chinese hamster ovary cells (CHO, Urlaub et al., (1980) Proc. Natl. Acad. ScL USA 77:4216); mouse Sertoli cells (TM4, Mather (1980) Biol. Reprod. 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982) Annals N.Y. Acad. Sci. 383:44-68); MRC 5 cells; FS4 cells; and PER.C6™ (Crucell Nev.).

Host cells are transformed with the above-described expression or cloning vectors for antibody or immunoglobulin IgG4 fusion protein production and cultured in conventional nutrient media modified as appropriate for inducing promoters, selecting transformants, or amplifying the genes encoding the desired sequences.

(vii) Culturing the host cells. The host cells used to produce the antibody of this invention may be cultured in a variety of media. Commercially available media such as Ham's FI0 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) Meth. Enz. 58:44, Barnes et al., (1980) Anal. Biochem. 102:255, U.S. Pat. Nos. 4,767,704; 4,657, 866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Chimeric Antibodies

The antibody according to the invention may be a chimeric antibody. Chimeric antibodies are made by recombinant means by combining the variable light and heavy chain regions (VL and VH), obtained from antibody producing cells of one species with the constant light and heavy chain regions from another. Typically chimeric antibodies utilize rodent or rabbit variable regions and human constant regions, in order to produce an antibody with predominantly human domains. For example, a chimeric antibody comprises a variable region from a mouse antibody fused to a human constant region. The production of such chimeric antibodies is known in the art, and may be achieved by standard means (as described, e.g., in Morrison, Science 229:1202 (1985); Oi et al, BioTechniques 4:214 (1986); Gillies et al., (1989) *J. Immunol. Methods* 125:191-202; U.S. Pat. Nos. 5,807,715; 4,816,567 and 4,816,397).

Primatised Antibody

The term "primatized antibody" refers to an antibody comprising monkey variable regions and human constant regions. Methods for producing primatized antibodies are known in the art. See e.g., U.S. Pat. Nos. 5,658,570; 5,681, 722; and 5,693,780, Humanized and Human Antibodies Included within the scope of the invention are de-immunised antibodies that have sequence variations produced using methods described in, for example, Patent Publication Nos EP0983303, WO 00/34317 and WO 98/52976.

The term "human" antibodies includes antibodies having the amino acid sequence of a human immunoglobulin and include antibodies isolated from human immunoglobulin libraries or from animals transgenic for one or more human immunoglobulins as described, for example, in U.S. Pat. No. 5,939,598. Human antibodies can be made by a variety of methods known in the art including phase display using antibody libraries derived from human immunoglobulin sequences. See also WO 98/46645, WO 98/24893, WO98/ 16654, WO 96/34096, WO 96/33735 and WO 91/10741.

The antibodies of the present invention may be humanized antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, one or more Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature, 321: 522-525; Riechmann et al., (1988) Nature, 332:323-329; and Presta (1992) Curr Op Struct Biol, 2:593-59).

Methods for humanizing non-human antibodies can be essentially performed following the method of Winter and co-workers (Jones P T et al (1986) Nature 321(6069):522; Riechmann L et al (1988) Nature 332(6162):323-327; Verhoeyen M et al (1988) Science 239(4847):1534-1536. Generally, a humanized antibody has one or more amino acid residues introduced into it from a source which is non-human. These non-human amino acid residues are often referred to as "import" residues, which are typically taken from an "import" variable domain. Accordingly, such "humanized" antibodies are chimeric antibodies (U.S. Pat.

No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibodies can be humanized using a variety of techniques known in the art including, for example, CDR-grafting (EP 239400; PCT publication WO 91/09967; U.S. Pat. Nos. 5,225,539; 5,530,101; and 5,585,089), veneering or resurfacing (EP 592106; EP519596; Padlan E A v al (1991) Mol Immunol 28(4-5):489; Studnicka G M et al (1994) Protein Eng 7(6):805-14) and chain shuffling (U.S. Pat. No. 5,565,332).

In some instances residues within the framework regions of one or more variable regions of the human immunoglobulin are replaced by corresponding non-human residues (see for example, Queen U.S. Pat. Nos. 5,585,089; 5,693,761; 5,693,762 and 6,180,370.

The invention also extends to antibodies humanised according to the methods referred to as Superhumanization® described in U.S. Pat. Nos. 6,881,557 and 7,732,578. Briefly, these methods for humanised antibodies are based on selecting variable region framework sequences from human antibody genes by comparing canonical CDR structure types for CDR sequences of the variable region of a non-human antibody to canonical CDR structure types for corresponding CDRs from a library of human antibody sequences. Human antibody variable regions having similar canonical CDR structure types to the non-human CDRs form a subset of member human antibody sequences from which to select human framework sequences.

Also included within the scope of the invention are "veneered antibodies". The term veneered antibody refers to selective replacement of framework region residues with human framework region residues in order to provide a xenogenic molecule comprising an antigen-binding site which retains substantially all of the native framework region folding structure. Veneering techniques are based on the understanding that the ligand-binding characteristics of an antigen-binding site are determined primarily by the structure and relative disposition of the heavy and light chain CDR sets within the antigen-binding surface. By using veneering techniques, exterior (e.g. solvent accessible) framework region residues, which are readily encountered by the immune system, are selectively replaced with human residues to provide a hybrid molecule that comprises either a weakly immunogenic, or substantially non-immunogenic, veneered surface.

Human antibodies can also be produced using various techniques known in the art, including phage display libraries (Hoogenboom and Winter (1991) J Mol Biol, 227:381; Marks et al. (1991) J Mol Biol, 222:581). The techniques of Cole et al. and Boerner et al. are also suitable for the preparation of human monoclonal antibodies (Cole et al., Monoclonal Antibodies and Cancer Therapy, Alan R. Liss, p. 77 (1985) and Boerner et al. (1991) J Immunol, 147:86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016.

In another embodiment fully human antibodies are obtained by immunizing transgenic mice. One such mouse is obtained using XenoMouse™ technology (Abgenix; Fremont, Calif.) and is disclosed in U.S. Pat. Nos. 6,075,181; 6,091,001 and 6,114,598. Fully human antibodies are expected to minimise the immunogenic and allergic responses intrinsic to mouse or mouse-derivatized monoclonal antibodies and thus to increase the efficacy and safety of the administered antibodies.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (Jespers et al, Bio/technology 12:899-903 (1988)).

The antibodies may also be affinity matured using known selection and/or mutagenesis methods as are known in the art. Preferred affinity matured antibodies have an affinity which is five times, more preferably 10 times, even more preferably 20 or 30 times greater than the starting antibody (generally murine, humanized or human) from which the matured antibody is prepared.

An "affinity matured" antibody is one with one or more alterations in one or more CDRs thereof which result in an improvement in the affinity of the antibody for IL-5, compared to a parent antibody which does not possess those alterations. Marks et al (1991) J Mol Biol 222:581-597 describes affinity maturation by VH and VL domain shuffling.

Antibody Binding

The antibodies of the invention may be assayed for specific binding by any method known in the art. The immunoassays which can be used include but are not limited to competitive and non-competitive assay systems using techniques such as BIAcore analysis, FACS (Fluorescent Activated Cell Sorter) analysis, immunofluorescence, immunocytochemistry, western blots, radioimmunoassays, ELISA, sandwich immunoassays, immunoprecitation assays, precipitin reactions, gel diffusion precipitin reactions, immunodiffusion assays, agglutination assays, complement-fixation assays, immunoradiometric assays, fluorescent immunoassays, protein A immunoassays etc.

Immunoglobulin IgG4 Fusion Proteins

The present invention also provides fusion proteins comprising a bioactive molecule recombinantly fused or chemically conjugated (including covalent or non-covalent conjugations) to a modified human IgG4 Fc region or FcRn binding domain thereof and modified human IgG4 core hinge region sequence of the invention. The term fusion protein is often synonymous with the term "immunoadhesin". Without wishing to be bound by theory, it is believed that mutations of the immunoglobulin IgG4 fusion protein stabilize the hinge region and mutations in the Fc region increase the affinity for human FcRn. In a particular embodiment, the fusion protein comprises the amino acid sequence in SEQ ID NO:14, or a variant thereof lacking the C-terminal amino acid (lysine).

The bioactive molecule which is fused can be any polypeptide or synthetic drug known to one of skill in the art. Examples of suitable polypeptides include cytokines, cell adhesion molecules (e.g. CTLA4, CD2 and CD28), ligands (e.g. TNF-alpha, TNF-beta and anti-angiogenic factor), receptors and growth factors (e.g. PDGF, EGF, NGF and KGF), an enzyme, a chemokine, The bioactive molecule which can be fused may also be a nonproteinaceous polymer e.g. polyethylene glycol or polypropylene glycol.

Methods for producing the bioactive molecule or immunoglobulin IgG4 fusion proteins of the invention include standard recombinant techniques or protein synthetic techniques eg by use of an automated protein synthesiser. For example, a nucleic acid molecule encoding the bioactive molecule of the invention can be synthesised by conventional techniques including automated DNA synthesisers. Alternatively, PCR amplification of gene fragments can be carried out using anchor primers which give rise to complementary overhangs between two consecutive gene fragments which can subsequently be annealed and reamplified to generate a chimeric gene sequence. Moreover, a nucleic acid sequence encoding a molecule can be cloned into an expression vector containing the Fc region or FcRn binding domain thereof such that the molecule is linked in frame to the Fc region or FcRn binding domain thereof.

Methods for fusing or conjugating polypeptides to the constant regions of antibodies are known in the art (see for example, U.S. Pat. Nos. 5,336,603; 5,622,929; 5,359,046; 5,349,053; 5,447,851; 5,723,125; 5,783,181; 5,908,626; 5,844,096; 5,112,946; 7,955,590).

The nucleotide sequence encoding the bioactive molecule may be obtained for example from Genbank, and the nucleotide sequence encoding a constant domain may be determined by sequence analysis of mutants produced using techniques described herein. The nucleotide sequence encoding the fusion protein can be inserted into an appropriate expression vector.

Polynucleotides

The present invention also provides polynucleotides comprising a nucleotide sequence encoding the modified antibody, immunoglobulin construct or immunoglobulin IgG4 fusion protein of the invention and polynucleotide sequences that hybridise under high stringency thereto.

Assays for Half-Life of Antibodies, Immunoglobulin Constructs and Immunoglobulin IgG4 Fusion Proteins of the Invention The half-life of the antibody, immunoglobulin construct or immunoglobulin IgG4 fusion protein of the invention can be measured by pharmacokinetic studies (PK) according to the method described by Kim et al, Eur J of Immunol 24:542 (1994). According to this method radiolabelled modified immunoglobulin is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the modified immunoglobulin or fusion protein of the invention, the clearance rate in beta-phase is calculated and compared with that of the wild type or unmodified antibody, immunoglobulin construct or IgG4 fusion protein.

PK studies such as that described above can be performed in a humanized FcRn mouse model wherein the murine endogenous FcRn is knocked out and the human FcRn knocked in as described in Petkova S B et al., (2006) International Immunology 18(12):1759-1769.

It has recently been reported that enhanced antibody half-life can be correlated with improved in vivo activity (Zalevsky J et al., (2010) nature Biotechnology 28(2):157-159).

In order to compare the ability of the modified antibody, immunoglobulin construct or immunoglobulin IgG4 fusion protein to bind FcRn with that of wild-type $IgG_4$, the modified $IgG_4$ antibody, immunoglobulin construct or immunoglobulin IgG4 fusion protein comprising $IgG_4$ hinge region modification and heavy chain constant region modifications, and the wild type $IgG_4$ can be radio-labelled and reacted with FcRn-expressing cells in vitro. The radioactivity of the cell-bound fractions can then be counted and compared. The cells expressing FcRn used in this assay are preferably endothelial cell lines including mouse pulmonary capillary endothelial cells (B10, D2.PCE) derived from lungs of B10.DBA/2 mice and SV40 transformed endothelial cells (SVEC) (Kim et al., J. Immunol., 40:457-465, (1994)) derived from C3H/HeJ mice. However, other types of cells such as intestinal brush borders isolated from 10- to 14-day old suckling mice, which express sufficient number of FcRn can also be used. Alternatively, mammalian cells which express recombinant FcRn of a species of choice can also be utilised. After counting the radioactivity of the bound fraction of modified immunoglobulin or fusion protein or that of wild type $IgG_4$, the bound molecules can then be extracted with detergent and the precent release per unit number of cells can be calculated and compared.

Affinity of modified antibody, immunoglobulin construct or immunoglobulin IgG4 fusion for FcRn can be measured by surface Plasmon resonance (SPR) measurement using, for example, a BIAcore 2000 (BIAcore, Inc) as described (Popov et al., Mol. Immunol., 33:493-502 (1996); Karlsson et al., J. Immunol. Methods, 145:229-240 (1991), which are incorporated by reference). In this method, FcRn molecules are coupled to a BIAcore sensor chip (e,g, Cm5 chip by Pharmacia) and the binding of modified immunoglobulin or fusion protein to the immobilised FcRn is measured at a certain flow rate to obtain sensorgrams using BIA evaluation 2.1 software, based on which on- and off rates of the modified antibody, immunoglobulin construct or immunoglobulin IgG4 fusion protein to FcRn can be calculated.

Relative affinities of modified antibody, immunoglobulin construct or immunoglobulin IgG4 fusion protein and the wild type IgG4 for FcRn can also be measured by a simple competition binding assay. Unlabeled modified antibody/immunoglobulin construct/immunoglobulin IgG4 fusion protein or wild-type $IgG_4$ is added in different amounts to the wells of a 96 well plate in which FcRn is immobilised. A constant amount of radio-labeled wild type $IgG_4$ is then added to each well. Percent radioactivity of the bound fraction is plotted against the amount of unlabeled modified immunoglobulin/fusion protein or wild type $IgG_4$ and the relative affinity of the modified antibody/immunoglobulin construct/immunoglobulin IgG4 fusion protein can be calculated from the slope of the curve.

Furthermore, affinities of modified antibody/immunoglobulin construct/immunoglobulin IgG4 fusion protein, and the wild type $IgG_4$ for FcRn can also be measured by a saturation study and Scatchard analysis.

Transfer of modified antibody/immunoglobulin construct/immunoglobulin IgG4 fusion protein and the wild type $IgG_4$ for FcRn can be measured by in vitro transfer assay using radiolabeled $IgG_4$ and FcRn expressing cells and comparing the radioactivity of the one side of the cell monolayer with that of the other side. Alternatively, such transfer can be measured in vivo by feeding 10- to 14-day old suckling mice with radiolabeled, modified antibody/immunoglobulin construct/immunoglobulin IgG4 fusion protein protein and periodically counting the radioactivity in blood samples which indicates the transfer of the $IgG_4$ through the intestine to the circulation (or any other target tissue). To test the dose-dependent inhibition of the IgG transfer through the gut, a mixture of radiolabeled and unlabeled $IgG_4$ at certain ratio is given to the mice and the radioactivity of the plasma can be periodically measured (Kim et al, Eur J of Immunol 24:542 (1994)).

Pharmaceutical Compositions and Modes of Administration

The antibodies, immunoglobulin constructs or immunoglobulin IgG4 fusion proteins of the present invention are useful for parenteral, topical, oral, or local administration, aerosol administration, or transdermal administration, for prophylactic, or for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are known in the art.

The pharmaceutical compositions of this invention are particularly useful for parenteral administration, such as intravenous administration or administration into a body cavity or lumen of an organ or joint. The compositions for administration will commonly comprise a solution of the antibody, immunoglobulin construct or immunoglobulin IgG4 fusion protein of the present invention dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody, immunoglobulin construct or immunoglobulin IgG4 fusion protein of the present invention in these formulations can vary widely, and will be selected primarily based on fluid volumes, viscosities, body weight and the like in accordance with the particular mode of administration selected and the subject's needs.

For example, for parenteral administration the subject antibodies may be formulated in a unit dosage injectable form (solution, suspension, emulsion) in association with a pharmaceutically acceptable parenteral vehicle. Examples of such vehicles are water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

The antibodies, immunoglobulin constructs or immunoglobulin IgG4 fusion proteins of the present invention can be formulated for parenteral administration, e.g., formulated for injection via the intravenous, intramuscular, sub-cutaneous, transdermal, or other such routes, including peristaltic administration and direct instillation into a tumor or disease site (intracavity administration). Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions can be formulated into a sterile aqueous composition in a neutral or salt form. Solutions of the antibodies, immunoglobulin constructs or immunoglobulin IgG4 fusion proteins of the present invention as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations can contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the antibodies, immunoglobulin constructs or immunoglobulin IgG4 fusion proteins of the present invention can be extensively dialyzed to remove undesired small molecular weight molecules, and/or lyophilized for more ready formulation into a desired vehicle, where appropriate. Sterile injectable solutions are prepared by incorporating the active ingredients in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredients, plus any additional desired ingredient from a previously sterile-filtered solution thereof.

Suitable pharmaceutical compositions in accordance with the invention will generally include an amount of the antibody, immunoglobulin construct or immunoglobulin IgG4 fusion protein of the present invention admixed with an acceptable pharmaceutical diluent or excipient, such as a sterile aqueous solution, to give a range of final concentrations, depending on the intended use. The techniques of preparation are generally known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein.

Upon formulation, the antibody, immunoglobulin construct or immunoglobulin IgG4 fusion protein of the present invention will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver antibodies, immunoglobulin constructs or immunoglobulin IgG4 fusion proteins of the present invention.

In some embodiments, liposomes and/or nanoparticles may also be employed with the active ingredients. The formation and use of liposomes is generally known to those of skill in the art. Liposomes can be formed from phospholipids that are dispersed in an aqueous medium and spontaneously form multilamellar concentric bilayer vesicles (also termed multilamellar vesicles (MLVs). MLVs can generally have diameters of from 25 nm to 4 µm. Sonication of MLVs results in the formation of small unilamellar vesicles (SUVs) with diameters in the range of 200 to 500 angstrom, containing an aqueous solution in the core. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

International Publication No. WO/2002/080967 describes compositions and methods for administering aerosolized compositions comprising antibodies for the treatment of, e.g., asthma, which are also suitable for administration of an antibody of the present invention.

The dosage of the antibody, immunoglobulin construct or immunoglobulin IgG4 fusion protein of the invention can be determined by a person skilled in the art. The dosage will, however depend upon the extent to which the in vivo half-life of the modified immunoglobulin or fusion protein has been increased. Further, the dosage and frequency of administration of antibodies or fusion proteins according to the invention may be reduced also by enhancing uptake and tissue penetration (e.g. into the lungs) by modifications such as, for example, lipidation.

Treatment with the antibodies, immunoglobulin constructs or immunoglobulin IgG4 fusion proteins of the invention include single treatment or a series of treatments. The pharmaceutical composition of the invention may be administered once a week, twice a week, once every two weeks, once a month, or once every six weeks.

Use of Modified Antibodies, Immunoglobulin Constructs or Immunoglobulin IgG4 Fusion Proteins of the Invention The modified antibodies, immunoglobulin constructs and immunoglobulin IgG4 fusion proteins in the present invention can be used for various non-therapeutic purposes. They may be used as an affinity purification agent. They may also be useful in diagnostic assays, such as detecting expression of an antigen of interest in specific cells, tissues, or serum. For diagnostic applications, the antibodies typically will be labeled with a detectable moiety, including radioisotopes, fluorescent labels, and various enzyme substrate labels. The antibodies may also be employed in any known assay method, such as competitive binding assays, direct and indirect sandwich assays, and immunoprecipitation assays. The antibodies, immunoglobulin constructs and immunoglobulin IgG4 fusion protein may also be used for in vivo diagnostic assays. Generally, the antibodies, immunoglobulin constructs and immunoglobulin IgG4 fusion protein are labeled with a radionucleotide so that the antigen or cell expressing it can be localized using immunoscintigraphy.

Use of Anti-IL-5 Antibodies in Therapy

A general feature in the pathogenesis of asthma and other chronic allergic diseases has proven to be elevated numbers of eosinophils, especially in the bronchial mucosa of the lungs. Upon activation, eosinophils secrete a number of mediators that are actively involved in the inflammatory airway response. In the activation of eosinophils, interleukin 5 (IL-5) plays an important role.

IL-5 is a cytokine found in many mammalian species and among others both the human and murine gene for IL-5 have been cloned. The human gene consists of four exons with three introns positioned at chromosome 5 and codes for a 134 amino acid N-terminal leader sequence. The active IL-5 is a homo-dimer and the 3-dimensional structure of recombinant hIL-5 has been determined by X-ray crystallography. The receptor for IL-5 is primarily present on eosinophils and it is composed of an alpha chain and a beta chain. The alpha chain of the receptor is specific for IL-5 and the beta chain, which assures high affinity binding and signal transduction, is shared with the hetero-dimer receptors for IL-3 and GM-CSF.

IL-5 is mainly secreted by fully differentiated Th2 cells, mast cells and eosinophils. It has been shown to act on eosinophils, basophils, cytotoxic T lymphocytes and on murine B cells.

The action of IL-5 on eosinophils include chemotaxis, enhanced adhesion to endothelial cells, and activation of terminal differentiation of the cells. Furthermore, it has been demonstrated that IL-5 prevents mature eosinophils from apoptosis. These findings have contributed to the concept of IL-5 being the most important cytokine for eosinophil differentiation.

While current treatment of asthma involves corticosteroids, it is envisioned that future treatment of asthma as well as other conditions mediated by eosinophils will include anti-IL-5 antibodies. Inappropriate secretion of cytokines and other effector molecules from eosinophils causes damage and dysfunction to the surrounding tissue. End-organ damage resulting from eosinophil infiltration and activation represents a common pathogenic component of several disease states, including atopic diseases and hypereosinophilic syndromes (HES). There is clearly a need for therapies which reduce eosinophil numbers in humans.

Antibodies, Immunoglobulin Constructs, and Immunoglobulin IgG4 Fusion Proteins of Invention in Treatment or Prevention of Disorders The modified antibodies, immunoglobulin constructs and immunoglobulin IgG4 fusion proteins have various therapeutic applications. The modified antibodies, immunoglobulin constructs and immunoglobulin IgG4 fusion proteins may be used to treat a subject suffering from, or predisposed to, a disease or disorder, who could benefit from administration of the modified antibodies. The conditions that can be treated with the antibodies include cancer; inflammatory conditions such as asthma; autoimmune diseases; and viral infections, etc The cancers that can be treated by the antibodies, immunoglobulin constructs and immunoglobulin IgG4 fusion proteins described herein include, but are not limited to, breast cancer, squamous cell cancer, small cell lung cancer, non-small cell lung cancer, gastrointestinal cancer, pancreatic cancer, glioblastoma, cervical cancer, ovarian cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and various types of head and neck cancer.

The autoimmune diseases include, but are not limited to, Addison's disease, autoimmune diseases of the ear, autoimmune diseases of the eye such as uveitis, autoimmune hepatitis, Crohn's disease, diabetes (Type I), epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatoid arthritis, sarcoidosis, scleroderma, Sjogren's syndrome, spondyloarthropathies, thyroiditis, ulcerative colitis, and vasculitis.

The present invention also includes methods for treating diseases characterised by eosinophilia. Asthma is a key target for the inventive method but also other chronic conditions such as multiple allergy, allergic rhinitis, and eosinophilic oesophagitis are suitable targets for treatment. Thus an embodiment of the method of the invention comprises treating and/or preventing and/or ameliorating asthma or other chronic allergic conditions characterised by eosinophilia comprising administration of an anti-IL-5 antibody which down regulates IL-5 activity to such an extent that the number of eosinophil cells is significantly reduced.

In the present context a significant reduction in eosinophil cell numbers is at least 20% compared to the eosinophil number prior art treatment, but higher percentages are contemplated, such as at least 30%, at least 40%, at least 50%, at least 60%, at least 70%, at least 80% and even at least 90%. The reduction may be systemic, or, more often locally, e.g. the lungs.

Eosinophil numbers are determined by methods known in the art, typically using microscopy of a suitable sample bronchioalveolar lavage (BAL) fluid and counting the number of eosinophil cells manually under microscope. Alternatively, eosinophil numbers can be counted using flow cytometry capable of distinguishing eosinophils.

The modified anti-CD33 antibodies of the invention are particularly useful in the treatment of cancer, more particularly myeloid leukemia. The present invention also encompasses an anti-CD33 which has been modified according to the invention to increase it half-life, conjugated to calicheamicin (Hamann P R et al., (2002) Bioconj Chem. 13(1):40-6) The anti-CD33-calicheamicin conjugate can be used to treat acute myeloid leukemia.

Utility of Non-Immunostimulatory Antibodies

The antibodies, immunoglobulin constructs and immunoglobulin IgG4 fusion proteins of the invention comprise a modified human IgG4 Fc region or FcRn binding domain thereof and a modified human IgG4 core hinge region sequence. It is known in the art that the isotype of the antibody constant domain influences the effector functions of the antibody. Of the various human immunoglobulin classes, only human IgG1, IgG2, IgG3 and IgM are known to activate complement; and human IgG1 and IgG3 mediate antibody dependent cell cytotoxicity (ADCC) more effectively than IgG2 and IgG4. Since the immunoglobulins and fusion proteins of the present invention comprise IgG4 constant region sequences, they are unable to activate the complement cascade or ADCC activity and hence any undesired NK-cell or T-cell activation. Accordingly, they are particularly amenable to allergic conditions such as asthma where it is not desirable to provoke activation of cells which may only exacerbate the condition.

IgG4 antibodies differ functionally from other IgG subclasses in their anti-inflammatory activity, which includes a poor ability to induce complement and cell activation because of low affinity for C1q (the q fragment of the first component of complement) and Fc gamma receptors. Consequently, IgG4 has become the preferred subclass for immunotherapy, in which recruitment of host effector function is undesirable.

Anti-IL-5 Antibodies

The present invention extends to antibodies, immunoglobulin constructs or immunoglobulin IgG4 fusion proteins comprising variable region sequences of light and heavy chains of known IL-5 antibodies joined to a modified human IgG4 Fc region and modified human IgG4 hinge region according to the present invention. Several examples of anti-IL-5 antibodies are described in U.S. Pat. Nos. 5,683,892; 5,693,323; 5,783,184; 5,851,525; 6,129,913; 5,096,071; 6,056,957 and 6,451,982. In addition, humanised anti-IL-5 antibodies CTIL-5-10gH/-gL6 (as described in U.S. RE39,548E), herein referred to as humanized 39D10 or hu39D10) and mepolizumab are particularly suitable for modification according to the present invention.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

Synergistic Effect of Substitutions

The present inventors have found that the YTE substitutions (that is, M252Y, S254T and T256E mutations) in an $IgG_4$ immunoglobulin or antibody Fc region, when combined with the S228P hinge region mutation in an $IgG_4$ antibody, synergistically increased half-life of the modified IgG$_4$ antibody in vivo. This was demonstrated for two different antibodies which bind to two different, unrelated antigens, as described in the examples.

In particular, the inventors found that while the YTE substitutions increased the affinity of the modified antibodies for human FcRn, the further inclusion of the S228P modification to the hinge region produced no further effect on antibody affinity for the FcRn. This is not entirely unexpected given that this region does not interact with the FcRn. It therefore would have been predicted that there would no synergy with regard to the S228P substitution and YTE substitutions. Because any modification in a human protein-based drug (including a protein comprising a human antibody constant region) increases the risk of inducing an anti-drug immune response in a patient, the general practice is to limit the number of such mutations to limit the presumably additively increased risk of each such mutation with respect to inducing such immune responses against the drug. However, due to the surprising results described herein that combination of the two classes of modifications (Fc modifications and hinge modifications) results in a supra-additive effect on increasing the circulating half-life of IgG4 antibodies, the benefits of combining these two classes of mutations may outweigh the theoretical disadvantages relating to increasing the incidence of promoting anti-drug immune reactions. The advantages of increasing half-life of a molecule will be immediately evident to the person skilled in the art. Such benefits include lower dosing and/or frequency of administration which lowers the risk of adverse events in a subject and reduces costs. Accordingly, such immunoglobulins with increased half-life are of significant pharmaceutical importance.

All references or documents referred to herein are considered to be incorporated by reference in their entirety.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

EXAMPLE 1

Materials and Methods
Generation of hu39D10 and its Variants

The gene encoding the human IgG4 heavy chain constant region was isolated from the Quickclone cDNA Library (Clontech, Mountain View, Calif.) and cloned into the pTT5 expression vector (Durocher et al, Nucleic Acids Research vol 30, No. 2, pp e9). To introduce the mutations described above in the Fc domain, a set of two primers of complementary sequence with one or more mutations were synthesized and used for PCR-based site-directed mutagenesis. The Ig kappa expression vector was constructed by similar means. The DNA fragments encoding the hu39D10 variable regions (FIG. 1) were reverse designed from the published protein sequences (U.S. RE39,548E), using 18 (heavy chain) or 16 (light chain) oligonucleotides by PCR-based gene-assembly. The fragments were cloned into the expression vectors using restriction sites integrated into the vectors for cloning. The final amino acid sequence for the hu39D10 heavy and light chains is shown in FIG. 1. The figure also shows the sequence of hu39D10 with the 4 amino acid substitutions (YTE+S228P, SEQ ID NO:6).

Expression and Purification of Hu39D10 and Variants pTT5 expression vectors for hu39D10 and its variants were transfected into HEK293 6E cells according to Durocher et al, Nucleic Acids Research vol 30, No. 2, pp e9. After 6 days of transfection, the culture media was isolated and then subjected to affinity purification using Protein G-agarose beads (GE Healthcare Life Sciences, Piscataway, N.J.).

Generation of FcRn/$\beta_2$ Microglobulin Complex Expression Constructs

The DNA fragments encoding human FcRn and $\beta_2$ microglobulin were isolated from cDNA synthesized with human Universal RNA (BioChain, Hayward, Calif.), a pool of human total RNA, using a Superscript III First-strand Synthesis kit (Invitrogen, Carlsbad, Calif.). The extracellular domain of FcRn (amino acid 24-290) and the mature part of $\beta_2$ microglobulin (amino acid 21-119) were cloned into the pTT5 expression vector individually. The sequences of the human FcRn extra cellular domain and $\beta_2$ microglobulin are shown FIG. 2 and FIG. 3, respectively.

Expression and Purification of FcRn/$\beta_2$ Microglobulin Complex

The pTT5 expression vectors for producing human FcRn and $\beta_2$ microglobulin were co-transfected into HEK293 6E cells. Six days after the transfection, the culture media was isolated and then subjected to affinity purification using IgG-Sephasore beads (GE Healthcare Life Sciences, Piscataway, N.J.).

ELISA to Measure the Affinity of hu39D10 and Variants to FcRn/$\beta_2$ Microglobulin Complex Maxisorp 96-well plates (Thermo Fisher Scientific, Rochester, N.Y.) were coated with 5 ug/ml anti-$\beta_2$ microglobulin monoclonal antibody. Wells were then washed with PBS and treated with Superblock blocking solution (Thermo Fisher Scientific, Rockford, Ill.). Then, the FcRn/$\beta_2$ microglobulin complex was diluted to 5 ug/ml in SPBS6T (50 mM sodium phosphate buffer pH 6.0, 150 mM NaCl, 0.05% Tween-20) and added to allow for capture by the coated anti-$\beta_2$ microglobulin antibody for 60 min at room temperature. Wells were then washed by SPBS6T and then exposed to hu39D10 or its variants in SPBS6T and incubated for 60 min at room temperature. The hu39D10/FcRn complex formed by the incubation was probed with an F(ab')2 fragment of an anti-human kappa HRP conjugate (SourthernBiotechnology, Birmingham, Ala.; 1/5000 dilution in SPBS6T) for 30 min at room temperature. After washing with SPBS6T, 100 ul of TMB (Sigma) was loaded into each well for signal detection. Then, 50 ul of 2N sulfuric acid was added to stop color development, and then A450 was measured in a Vmax plate reader (Molecular Devices, Sunnyvale, Calif.). The affinity of the IgG variants to FcRn was calculated and plotted using Prism software by GraphPad Software (La Jolla, Calif.).

Results and Conclusions

As shown in FIG. 4, the affinity of hu39D10 for human FcRn (EC50=3.8 nM) was increased by 4.7 times by making the YTE mutations (to EC50=0.81 nM). The further addition of the S228P mutation had no effect on FcRn affinity (EC50=0.81 nM, the same as for hu39D10 with the YTE mutations). This result was not unexpected since the S228P mutation is far away from the region of the Fc that interacts with FcRn. Based on this result, one would not expect any synergy between the YTE and S228P mutations on circulating half-life.

EXAMPLE 2

PK Study

The mouse PK study was performed by the Jackson Laboratory—West (Sacramento, Calif.) with mice that have their endogenous FcRn knocked out but have the human FcRn knocked in (the 4919 Tg276 hemizygous mouse model described in Petkova et al, (2006) International Immunology vol. 18, No. 12, pp. 1759-1769). At day 0, seven mice in each group received hu39D10 or its variants intraperitoneally (IP) (200 ug). Each mouse was bled from the retro orbital sinus at 2, 12, 24 hours and 2, 4, 7, 10, 14, 18, 21 and 28 days to prepare plasma samples.

ELISA to Measure hu39D10 and Variants in Plasma Samples

Maxisorp 96-well plates (Thermo Fisher Scientific, Rochester, N.Y.) were coated with recombinant IL-5 (the hu39D10 antigen; R&D Systems, Minneapolis, Minn.) at 2 ug/ml in PBS overnight in a refrigerator. Wells were then washed with PBS and blocked with 200 ul Superblock blocking solution (Thermo Fisher Scientific, Rockford, Ill.) for 30 min to minimize nonspecific binding. The plasma samples were then diluted to 1/50 in PBS-Tween20 (PBST) and loaded into the IL-5-coated wells. In addition, a recombinant hu39D10 standard was diluted in PBST with 2% mouse serum (Sigma-Aldrich, St. Louis, Mo.) and loaded into coated wells to make a standard curve for the quantification. After a 60 min incubation at room temperature, wells were washed with PBST and then an anti-human Fc-HRP conjugate (Sigma-Aldrich, St. Louis, Mo., 1/1000 dilution in PBST) was added and incubated for 30 min at room temperature. Wells were then washed with PBST. For signal detection, 100 ul of TMB (Sigma-Aldrich, St. Louis, Mo.) was loaded into each well. Then, 50 ul of 2N sulfuric acid was added to stop color development, and then A450 was measured in a Vmax plate reader (Molecular Devices, Sunnyvale, Calif.). The concentration of hu39D10 and the variants in the plasma was calculated using the Prism (GraphPad Software, La Jolla, Calif.) software and using the hu39D10 standard curve. For each mouse, the relative concentration of hu39D10 compared to the concentration measured at Day 1 (defined as 100%) was plotted as a function of time. The half-life of hu39D10 or its variants in individual animals was also calculated using the software, assuming an exponential decay and an asymptote of zero. For the half-life calculation of the variant with combined mutations (S228P+YTE), two outlier results (that is the results from two of the mice), which increase the calculated half-life, were excluded for the calculation of average half-life.

Results and Conclusions

Figure 5:
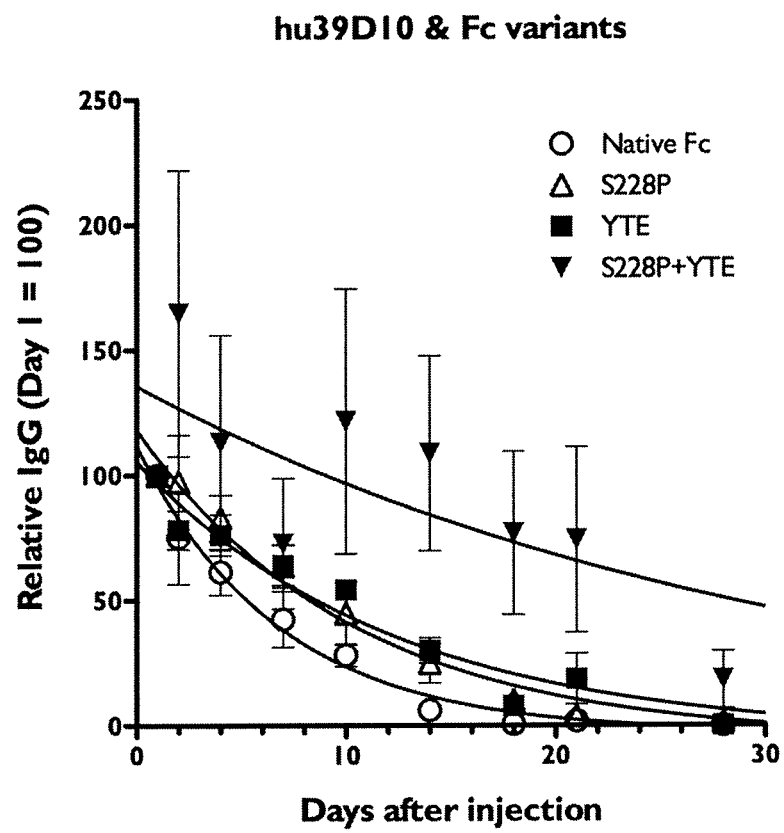
FIG. 5 shows a PK study in mice with humanised FcRn, i.e. mice which are deleted for the endogenous FcRn gene but have ectopic expression of the human counterpart. At day 0, mice received hu39D10 or variants containing either the YTE substitutions alone, the hinge substitution (S228P) alone or both types of substitutions. Each mouse was bled from the retro orbital sinus at 2, 12, 24 hours and 2, 4, 7, 10, 14, 18, 21 and 28 days. Plasma samples were analysed for humanised antibody concentration. Antibody levels are expressed as a percent of the level at the 24 hour time point in the same mouse.

As shown in FIG. 5, the serum half-life of hu39D10 with the S228P mutation ($t\frac{1}{2}$=6.5 days) was increased by 42% compared to hu39D10 with unmodified Fc ($t\frac{1}{2}$=4.6 days). The YTE mutations also show significant enhancement of serum half-life by 75% ($t\frac{1}{2}$=8.0 days). Surprisingly, when combined, the S228P and YTE mutations further elongated the circulating half-life synergistically (to $t\frac{1}{2}$=13.3 days). The addition of the S228P mutation to the YTE mutations increased the circulating half-life by 66% (or by 5.3 days) relative to the YTE alone, whereas the half-life increase of S228P in the context of non-YTE mutated IgG4 resulted in only a 42% (1.9 day) increase. Absent synergy between the S228P and YTE mutations, the S228P mutation would cause the same or a reduced proportional increase in the half life in the context of the YTE-mutated hu39D10 as it does in the context of the non-YTE mutated hu39D10, yielding a half-life of no greater than 11 days for hu39D10 with both the YTE and S228P mutations.

Due to this synergy, it is concluded that it is beneficial to combine the YTE and S228P mutations in the same molecule in order to achieve a very long half-life for an antibody (or Fc fusion protein)-based drug, despite the increased chance of promoting anti-drug immune responses due to an increased number of mutations in the Fc constant region.

EXAMPLE 3

Materials and Methods

Generation of huMab195 and its Fc Variants

The DNA fragments encoding the CD33-binding antibody huMab195 variable regions (FIG. 6), were reverse engineered from the published protein sequences (U.S. Pat. No. 5,693,761), using 18 (heavy chain) and 18 (light chain) oligonucleotides by PCR-based gene assembly. The heavy and light chain variable region fragments were then cloned into the human IgG4 (native and variant) expression vectors described in the previous section to create an IgG4/kappa version of huMab195, with native IgG4 constant domain sequence, or versions containing the S228P mutation, the YTE mutations, or both the S228P and the YTE mutations. The sequence of huMab195 IgG4 heavy chain with both the S228P and YTE mutations is shown in FIG. 6, as is the light chain sequence.

Expression and Purification of huMab195 and Variants

The pTT5 expression vectors for huMab195 and its variants were transfected into HEK293 6E cells in order to produce the various IgG4 proteins, as described in Example 2. These proteins were then purified using Protein G-agarose beads as in Example 2.

Generation of Human CD33 Extracellular Domain

A DNA fragment encoding the human CD33 extracellular domain (hCD33 ECD, amino acid 1-258, including leader sequence) was amplified from the Quickclone human cDNA Library (Clontech, Mountain View, Calif.). DNA encoding a $(His)_6$ tag followed by a thrombin cleavage site (Leu-Val-Pro-Arg-Gly-Ser) was added to the 3' end of the hCD33 ECD fragment by PCR using a primer carrying these sequences. The his6-tagged hCD33 ECD-encoding DNA fragment was then ligated to a human IgG1 Fc-encoding DNA fragment by PCR (hCD33 ECD-Fc) and cloned into the pTT5 expression vector. The protein sequence of the hCD33 ECD-Fc is shown in FIG. 7.

Expression and Purification of Human CD33 Extracellular Domain

The pTT5 expression vector encoding the hCD33 ECD-Fc fusion protein was transfected into HEK293 6E cells, and then the culture media was isolated and subjected to affinity purification using Protein G-agarose beads (GE Healthcare Sciences, Piscataway, N.Y.). To isolate hCD33 ECD, the purified fusion protein was treated with thrombin (EMD Chemicals, San Diego, Calif.) to remove the Fc portion. Then, the hCD33 ECD was isolated by NiNTA-agarose (Qiagen GmbH, Hilden, Germany) affinity chromatography.

PK Study

The mouse PK study was performed by the Jackson Laboratory—West (Sacramento, Calif.) with mice that have their endogenous FcRn knocked out but have the human FcRn knocked in (the 4919 Tg276 hemizygous mouse model described in Petkova et al, International Immunology vol. 18, No. 12, pp. 1759-1769). At day 0, seven mice in each group received huMab195 or its variants intraperitoneally (IP) (200 ug). At 2, 12 and 24 hours and 2, 4, 7, 10, 14 days after the administration, each mouse was bled to prepare plasma samples.

ELISA to Measure huMAb195 and Variants in Plasma Samples

Maxisorp 96-well plates (Thermo Fisher Scientific, Rochester, N.Y.) were coated with recombinant hCD33 ECD at 2 ug/ml in PBS solution. Wells were then washed with PBS and blocked with Superblock blocking solution (Thermo Fisher Scientific, Rockford, Ill.). The plasma samples were diluted to 1/50 in PBS-Tween20 (PBST) and then loaded into the hCD33 ECD-coated wells. In parallel, known concentrations of recombinant huMab195 standards were diluted in PBST with 2% mouse serum (Sigma-Aldrich, St. Louis, Mo.) and loaded into coated wells to make a standard curve for the quantification. After a 60 min incubation at room temperature, wells were washed with PBST and then an anti-human kappa fragment HRP-conjugate (Invitrogen, Carlsbad, Calif.; 1/2000 dilution in PBST) was added and incubated for 30 min. After washing the wells, the signals were developed, measured and analysed as described in Example 2.

RESULTS AND CONCLUSIONS

Figure 8:
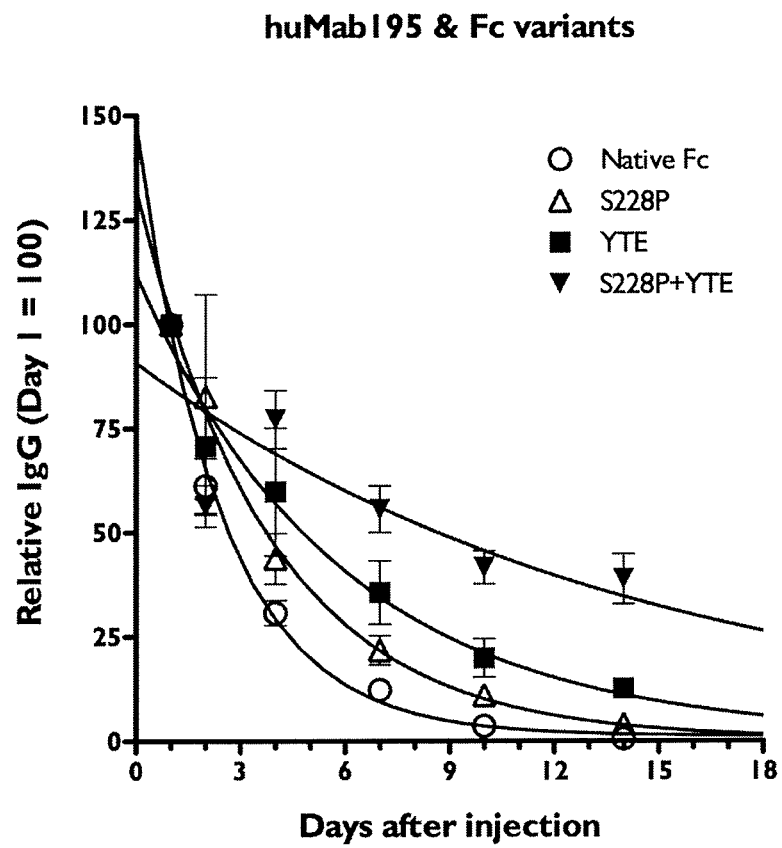
FIG. 8 shows a PK study in mice with humanised FcRn, i.e. mice which are deleted for the endogenous FcRn gene but have ectopic expression of the human counterpart. At day 0, mice received huMab195 with a native IgG4 Fc domain or variants containing either the YTE substitutions alone, the hinge substitution (S228P) alone or both types of substitutions. Each mouse was bled from the retro orbital sinus at 2, 12, 24 hours and 2, 4, 7, 10 and 14 days. Plasma samples were analysed for humanised antibody concentration. Antibody levels are expressed as a percent of the level at the 24 hour time point in the same mouse.

As shown in FIG. 8, the serum half-life of the huMab195 with the S228P mutation (t½=2.0 days) was increased by 26% compared to the huMAb195 with unmodified Fc (t½=1.6 days). The YTE mutations also show significant enhancement of serum half-life by 110% (t½=3.4 days). When the S228P and YTE mutations were combined, the half-life was further increased to 14 days, an increase of 312% compared to the YTE variant. Absent synergy, the maximum increase from the addition of the S228P mutation to the YTE-containing huMab195 would be 26%, resulting in a half-life of 4.3 days, which is significantly shorter than the observed 14 days. This second example confirms the observation that the S228P and YTE modifications to human IgG4 antibodies are synergistic with respect to their effect on increasing the circulating half lives of IgG4 antibodies in subjects with a human FcRn. Such synergy may justify the use of these two modifications in same protein, in spite of the potential for increased immunogenicity.

The invention claimed is:

1. A modified antibody, immunoglobulin construct, or immunoglobulin IgG4 fusion protein that specifically binds to Interleukin 5 (IL-5), comprising the complementarity determining regions (CDRs) of the heavy chain variable domain amino acid sequence of SEQ ID NO: 7, and the CDRs of the light chain variable domain amino acid sequence of SEQ ID NO: 8,
- a human IgG4 Fc region comprising the amino acid substitutions M252Y, S254T and T256E numbered according to the EU index as in Kabat, and
- a human IgG4 core hinge region comprising the amino acid substitution S228P according to the EU index as in Kabat;
    - wherein the combination of the amino acid substitutions S228P, M252Y, S254T and T256E results in a synergistic increase in the circulating half-life of the modified antibody, immunoglobulin construct, or immunoglobulin IgG4 fusion protein in vivo as compared to the circulating half-life in vivo of the antibody, immunoglobulin construct, or immunoglobulin IgG4 fusion protein which has been modified to comprise the amino acid substitutions S228P or M252Y, S254T and T256E.

2. The modified antibody, immunoglobulin construct, or immunoglobulin IgG4 fusion protein according to claim 1, wherein the modified antibody, immunoglobulin construct, or immunoglobulin IgG4 fusion protein comprises the heavy chain constant domain amino acid sequence of SEQ ID NO:6, the heavy chain variable domain amino acid sequence of SEQ ID NO:7, and a light chain comprising the amino acid sequence of SEQ ID NO: 8.

3. The isolated antibody, immunoglobulin construct, or immunoglobulin IgG4 fusion protein according to claim 1, wherein the modified antibody, immunoglobulin construct, or immunoglobulin IgG4 fusion protein comprises a light chain comprising the amino acid sequence of SEQ ID NO:8.

4. The modified antibody, immunoglobulin construct, or immunoglobulin IgG4 fusion protein according to claim 1, wherein the modified antibody, immunoglobulin construct, or immunoglobulin IgG4 fusion protein is recombinantly-fused or chemically-conjugated to a moiety.

5. The modified antibody, immunoglobulin construct, or immunoglobulin IgG4 fusion protein according to claim 4, wherein the moiety is selected from the group consisting of a therapeutic agent, a cytotoxin, a radioisotope, an immunomodulatory agent, an anti-angiogenic agent, an anti-neovascularization and/or vascularization agent, a toxin, an anti-proliferative agent, a pro-apoptotic agent, a chemotherapeutic agent, and a therapeutic nucleic acid.

6. A composition, comprising the modified antibody, immunoglobulin construct or immunoglobulin IgG4 fusion protein according to claim 1 and a pharmaceutically acceptable excipient or carrier.

* * * * *